US012767698B2

(12) United States Patent
Guillonneau et al.

(10) Patent No.: US 12,767,698 B2

(45) Date of Patent: Oct. 20, 2026

(54) ISOLATED MHC-DERIVED HUMAN PEPTIDES AND USES THEREOF FOR STIMULATING AND ACTIVATING THE SUPPRESSIVE FUNCTION OF $CD8^{+}CD45RC^{LOW}$ TREGS

(71) Applicants: INSERM (INSTITUT NATIONAL DE LA SANTÉ ET DE LA RECHERCHE MÉDICALE), Paris (FR); UNIVERSITÉ DE NANTES, Nantes (FR)

(72) Inventors: Carole Guillonneau, La Chevrolière (FR); Séverine Bezie, Nantes (FR); Elodie Picarda, New York, NY (US)

(73) Assignees: INSERM (INSTITUT NATIONAL DE LA SANTÉ ET DE LA RECHERCHE MÉDICALE), Paris (FR); UNIVERSITÉ DE NANTES, Nantes (FR)

( * ) Notice: Subject to any disclaimer, the term of this patent is extended or adjusted under 35 U.S.C. 154(b) by 1031 days.

(21) Appl. No.: 17/312,161

(22) PCT Filed: Dec. 13, 2019

(86) PCT No.: PCT/EP2019/085205

§ 371 (c)(1),
(2) Date: Jun. 9, 2021

(87) PCT Pub. No.: WO2020/120786

PCT Pub. Date: Jun. 18, 2020

(65) Prior Publication Data

US 2022/0064260 A1 Mar. 3, 2022

(30) Foreign Application Priority Data

Dec. 14, 2018 (EP) .................................... 18306692

(51) Int. Cl.

| | |
|---|---|
| ***A61K 39/00*** | (2006.01) |
| ***A61K 40/11*** | (2025.01) |
| ***A61K 40/22*** | (2025.01) |
| ***A61K 40/41*** | (2025.01) |
| ***A61K 40/42*** | (2025.01) |
| ***A61K 47/68*** | (2017.01) |
| ***A61K 47/69*** | (2017.01) |
| ***C07K 14/705*** | (2006.01) |
| ***C12N 5/0783*** | (2010.01) |

(52) U.S. Cl.

CPC ...... *C07K 14/70539* (2013.01); *A61K 39/001* (2013.01); *A61K 40/11* (2025.01); *A61K 40/22* (2025.01); *A61K 40/418* (2025.01); *A61K 47/6811* (2017.08); *A61K 47/6835* (2017.08); *C12N 5/0637* (2013.01); *A61K 2039/577* (2013.01); *A61K 2039/6056* (2013.01); *C07K 2319/00* (2013.01); *C12N 2501/056* (2013.01); *C12N 2501/2302* (2013.01); *C12N 2501/2315* (2013.01); *C12N 2501/51* (2013.01); *C12N 2501/515* (2013.01); *C12N 2502/1121* (2013.01)

(58) Field of Classification Search

None

See application file for complete search history.

(56) References Cited

U.S. PATENT DOCUMENTS

| | | | | |
|---|---|---|---|---|
| 10,105,425 | B2 * | 10/2018 | Guillonneau | A61K 39/001 |
| 10,137,181 | B2 * | 11/2018 | Guillonneau | A61K 35/17 |
| 2009/0004213 | A1 | 1/2009 | Singh et al. | |
| 2009/0311283 | A1 * | 12/2009 | Sette | A61K 31/7088 530/328 |
| 2009/0317428 | A1 | 12/2009 | Rammensee | |
| 2018/0251731 | A1 * | 9/2018 | Guillonneau | A61P 37/06 |

FOREIGN PATENT DOCUMENTS

| | | | |
|---|---|---|---|
| WO | 9320842 | A1 | 10/1993 |
| WO | 2005070090 | A2 | 8/2005 |
| WO | 2006037421 | A2 | 4/2006 |

(Continued)

OTHER PUBLICATIONS

HLA Nomenclature (2023, 2 pages) (Year: 2023).*

Weiczorek et al ( (Front. Immunol., 2017, article 292: 1-16) (Year: 2017).*

Celis et al (Mol. Immunol., 1994, 31(18): 1423-1436) (Year: 1994).*

(Continued)

*Primary Examiner* — Misook Yu

*Assistant Examiner* — Marianne Dibrino

(74) *Attorney, Agent, or Firm* — Maier & Maier, PLLC

(57) ABSTRACT

Isolated MHC-derived human peptides, particularly an isolated MHC-derived human peptide including a SDVGE-X-R (SEQ ID NO: 13) 7 amino acids motif that is selected from: NQEESVRFDSDVGEFR (Hpep 1—SEQ ID NO:1), NREEYARFDSDVGEFR (Hpep2—SEQ ID NO:2), NREEYVRFDSDVGEYR (Hpep4—SEQ ID NO:4) and any peptide with a length of 16 amino acids including the SDVGE-X-R (SEQ ID NO: 13) motif and having an amino acid sequence with at least 80, 85, 86, 87, 88, 90, 91, 92, 93, 94, 95, 96, 97, 98 or 99% identity with SEQ ID NO: 1, SEQ ID NO: 2 or SEQ ID NO: 4. Also, the use of these peptides in methods for inducing an immune tolerance, for preventing or reducing transplant rejection or graft versus host disease (GVHD), and in methods for isolating and expanding a population of $CD8^{+}CD45RC^{low}$ Tregs or for expanding a population of $CD8^{+}CD45RC^{low}$ Tregs and stimulating its immunosuppressive activity.

9 Claims, 4 Drawing Sheets

Specification includes a Sequence Listing.

(56) References Cited

FOREIGN PATENT DOCUMENTS

| | | | |
|---|---|---|---|
| WO | 2007140472 | A2 | 12/2007 |
| WO | 2014160465 | A2 | 10/2014 |
| WO | 2015150491 | A1 | 10/2015 |
| WO | 2015150492 | A2 | 10/2015 |
| WO | 2017042170 | A1 | 3/2017 |

OTHER PUBLICATIONS

Ochoa-Garay et al (Molec. Immunol., 1997, 34: 273-281 and Karin et al (J. Exp. Med. 1994, 180:2227-2237) (Year: 1997).*

Karin et al (J. Exp. Med. 1994, 180:2227-2237) (Year: 1994).*

Khan and Salunke (J. Immunol, 2014, 192: 5398-5405) (Year: 2014).*

Lloyd et al (Protein Engineering, Eng. Design & Selection, 2009, 22(3): 159-168) (Year: 2009).*

Edwards et al (JMB, 2008, 334: 103-118) (Year: 2008).*

UniProt Acc. No. A0A0A7CAL0, 1 page, 2025 (Year: 2025).*

Merriam-Webster dictionary (merriam-webster.com/dictionary/medicament, 2025, 7 pages) (Year: 2015).*

Merriam-Webster Dictionary (merriam-webster.com/dictionary/encode, 2025, 1 page) (Year: 2025).*

Chen and Ren (Immun. Res., 2012, 53: 182-190) (Year: 2012).*

Ellis et al. (Human Immunol. 2000, 61: 334-340) (Year: 2000).*

Niederlova et al. (Eur. J. Immunol., 2021, 51: 512-530, section spanning cols. 1-2 on p. 522) (Year: 2021).*

Picarda E. et al. "MHC-derived allopeptide activates TCR-biased CD8+ Tregs and suppresses organ rejection", Journal of Clinical Investigation, Jun. 2014, vol. 124, No. 6, pp. 2497-2512, doi: 10.1172/JCI71533.

Liu Z. et al. "Indirect Recognition of Donor MHC Class II Antigens in Human Transplantation", Clinical Immunology and Immunopathology, Mar. 1996, vol. 78, No. 3, pp. 228-235, doi: 10.1006/clin.1996.0034.

Van Denderen B. et al. "Identification of immunodominant donor MHC peptides following rejection and donor strain transfusion-induced tolerance of heart allografts in adult rats." European Journal of Immunology, May 2001, vol. 31, No. 5, pp. 1333-1339, doi: 10.1002/1521-4141(200105)31:5<1333::AID-IMMU1333>3.0.CO;2-1, 8 pages.

Lovitch S. B. et al. "APCs Present Abeta(k)-Derived Peptides That Are Autoantigenic to Type B T Cells." Journal of Immunology, Apr. 15, 2003, vol. 170, No. 8, pp. 4155-4160, doi: 10.4049/jimmunol.170.8.4155, 7 pages.

Freed J. H. et al. "MHC Class II-Bound Self-Peptides from Autoimmune MRL/lpr Mice Reveal Potential T Cell Epitopes for Autoantibody Production in Murine Systemic Lupus Erythematosus." Journal of Immunology, May 1, 2000, vol. 164, No. 9, pp. 4697-4705, doi: 10.4049/jimmunol.164.9.4697, 10 pages.

Ballet C. et al. "Indirect CD4+ TH1 Response, Antidonor Antibodies and Diffuse C4d Graft Deposits in Long-Term Recipients Conditioned by Donor Antigens Priming." American Journal of Transplantation, Apr. 2009, vol. 9, No. 4, pp. 697-708, doi: 10.1111/j.1600-6143.2009.02556.x, 13 pages.

Michael M. et al. "Regulatory T Cells in Allogeneic Stem Cell Transplantation." Clinical and Developmental Immunology, 2013, vol. 2013, Article ID 608951, 10 pages, doi: 10.1155/2013/608951.

Speir J. A. et al. "Two Different, Highly Exposed, Bulged Structures for an Unusually Long Peptide Bound to Rat MHC Class I RT1-Aa." Immunity, Jan. 2001, vol. 14, No. 1, pp. 81-92, doi: 10.1016/s1074-7613(01)00091-7.

International Search Report issued on Feb. 7, 2020, in connection with corresponding International Application No. PCT/EP2019/085205; 6 pages.

* cited by examiner

| *name* | *sequence* | *length* | *identifier* |
|---|---|---|---|
| Hpep1 | NQEESVRFDSDVGEFR | 16 | SEQ ID NO: 1 |
| Hpep2 | NREEYARFDSDVGEFR | 16 | SEQ ID NO: 2 |
| Hpep3 | NREEYARFDSDVGVYR | 16 | SEQ ID NO: 3 |
| Hpep4 | NREEYVRFDSDVGEYR | 16 | SEQ ID NO: 4 |
FIG. 1
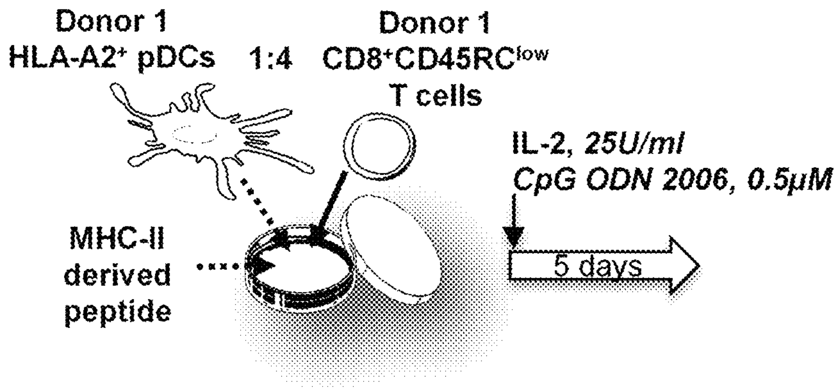
FIG. 2
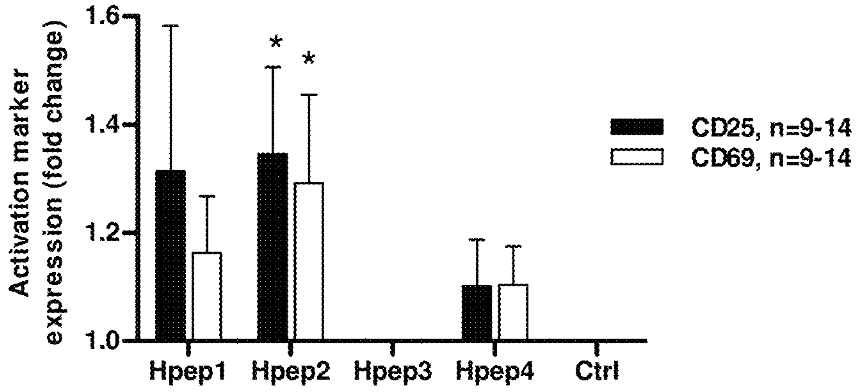
FIG. 3A

ISOLATED MHC-DERIVED HUMAN PEPTIDES AND USES THEREOF FOR STIMULATING AND ACTIVATING THE SUPPRESSIVE FUNCTION OF CD8$^+$CD45RC$^{LOW}$ TREGS

REFERENCE TO A SEQUENCE LISTING

In accordance with 37 CFR § 1.821(c), the present specification makes reference to a Sequence Listing submitted as an ASCII plain text file via the USPTO patent electronic filing system," 1385PCT_Corrected_Sequence_listing.txt". The .txt file was generated on Jun. 9, 2021, and is 3,327 bytes in size. The entire contents of the Sequence Listing are hereby incorporated by reference.

FIELD

The present invention relates to isolated MHC-derived human peptides and uses thereof for stimulating and activating the suppressive function of CD8$^+$CD45RC$^{low}$ Tregs.

BACKGROUND

Immunosuppressive regimens have significantly improved long-term graft survival in the last decades but they still cannot prevent the allograft from chronic graft dysfunction and they remain a significant obstacle for the welfare of transplanted patients. Thus, in the last years, improvement of allograft survival has stagnated, mainly because of chronic graft rejection, secondary effects and non-specific immunosuppression.

The identification in humans of regulatory cell populations actively controlling immune responses in transplantation with high suppressive capacity and specificity toward donor antigens has generated revolutionizing therapeutic strategies in a number of diseases with a deregulation of the regulatory T cells/effector T cells ratio (Treg/Teff). The establishment of cellular therapy with regulatory cells has recently emerged has a promising future therapy in autoimmunity as well as bone marrow and solid organ transplantation.

Several studies have demonstrated the importance of antigen recognition by the TCR for survival, stimulation of suppressive function and the superiority of such antigen-experienced Tregs. Phase I studies in graft versus host disease (GVHD) and solid organ transplantation have started with regulatory cells from different types (different CD4$^+$ Tregs, macrophages and DCs) without apparent toxicity, but to date, there are no clinical trials using CD8$^+$ Tregs despite abundant literature in animal models. One limitation for translation of CD8$^+$ Tregs in humans might be that Foxp3, a critical gene in the function of CD4$^+$ Tregs to efficiently restrain immune responses, is not clearly defined for CD8$^+$ Tregs and its expression according to other surface markers or cytokines and function has not been clearly demonstrated for CD8$^+$ Tregs in humans.

Recently a new population of highly suppressive human CD8$^+$CD45RC$^{low}$Tregs was identified (WO2017/042170). This population is characterized by expressing Foxp3 and producing IFNγ, IL-10, IL-34 and TGFβ to mediate their suppressive activity. Furthermore, a dominant MHC class II-derived antigens (called Du51) recognized by TCR-biased CD8$^+$ Tregs was identified in rats (WO2015/150492). Treatment of recipient rats with only antigens Du51 resulted in donor-specific allograft tolerance induction, highlighting the importance of the TCR/peptide/MHC interaction for CD8$^+$ Treg generation and function.

Now the inventors designed four 16aa peptides from four random human MHC class II alleles and tested individually these peptides in a 5-days culture assay using HLA-A2$^+$ pDCs and syngeneic CD8$^+$CD45RC$^{low}$ Tregs in presence of IL-2 and CpG. They observed that CD25 and CD69 expression was upregulated following incubation with the peptides. Furthermore, the inventors showed that expansion with antigen presenting cells (APCs) in presence of one peptide resulted in a 10-fold expansion of the CD8$^+$CD45RC$^{low}$ Tregs. Importantly, peptide expanded CD8$^+$CD45RC$^{low}$ Tregs were efficient at suppressing an allogeneic immune response similarly to fresh CD8$^+$CD45RC$^{low}$ Tregs. Accordingly, the present invention relates to isolated MHC-derived human peptides, uses thereof for inducing immune tolerance and for preventing or reducing transplant or graft rejection or graft versus host disease (GVHD), and uses thereof for stimulating and expanding CD8$^+$CD45RC$^{low}$ Tregs and for activating the suppressive function of CD8$^+$CD45RC$^{low}$ Tregs.

SUMMARY

The present invention relates to isolated MHC-derived human peptides and uses thereof for stimulating, expanding and activating the suppressive function of CD8$^+$CD45RC$^{low}$ Tregs. In particular, the present invention is defined by the claims.

The present invention thus relates to an isolated MHC-derived human peptide which comprises a SDVGE-X-R (SEQ ID NO: 13) 7 amino acids motif and which is selected from the group consisting of NQEESVRFDSDVGEFR (Hpep 1—SEQ ID NO:1), NREEYARFDSDVGEFR (Hpep2—SEQ ID NO:2), NREEYVRFDSDVGEYR (Hpep4—SEQ ID NO:4) and any peptide with a length of 16 amino acids comprising the SDVGE-X-R (SEQ ID NO: 13) motif and having an amino acid sequence with at least 80% identity with SEQ ID NO: 1, SEQ ID NO: 2 or SEQ ID NO: 4. In one embodiment, said peptide is NQEESVRFDSDVGEFR (Hpep 1—SEQ ID NO:1) or a peptide with a length of 16 amino acids comprising the SDVGE-X-R (SEQ ID NO: 13) motif and having an amino acid sequence with at least 80% identity with SEQ ID NO: 1.

The present invention also relates to a nucleic acid molecule that encodes the peptide of the invention. The present invention also relates to an immunoconjugate comprising an antibody conjugated or fused to the peptide of the invention. In one embodiment, said antibody is directed against a surface antigen of an antigen presenting cell (APC).

The present invention also relates to a nanoparticle comprising at least one peptide of the invention. In one embodiment, the nanoparticle is a liposome. The present invention also relates to a vaccine composition comprising the peptide of the invention, the immunoconjugate of the invention or the nanoparticle of the invention.

The present invention also relates to a MHC class I multimer loaded with the peptide of the present invention. The present invention also relates to an antibody that specifically binds to the peptide of the invention or to the MHC class I multimer of the invention.

The present invention also relates to the peptide of the invention, the immunoconjugate of the invention, the nanoparticle of the invention, or the vaccine composition of the invention for use as a medicament. The present invention also relates to the peptide of the invention, the immunoconjugate of the invention, the nanoparticle of the invention, or the vaccine composition of the invention for use in preventing or reducing transplant or graft rejection or graft versus host disease (GVHD) in a patient in need thereof.

The present invention further relates to a method for expanding a population of $CD8^+CD45RC^{low}$ Tregs and stimulating its immunosuppressive activity, comprising a step of culturing a population of $CD8^+CD45RC^{low}$ Tregs with a culture medium comprising the peptide of the invention in presence of a population of antigen presenting cells (APCs) or with a culture medium comprising the MHC class I multimer of the invention. In one embodiment, the antigen presenting cells are dendritic cells, monocytes and/or artificial antigen presenting cells (aAPCs).

The present invention also relates to a method for isolating and expanding a population of $CD8^+CD45RC^{low}$ Tregs specifically recognizing the peptide of the invention, comprising a step of isolating a population of $CD8^+CD45RC^{low}$ Tregs specifically recognizing the peptide of the invention by MHC/peptide multimer staining with the MHC class I of the invention, and then a step of expanding the isolated population of $CD8^+CD45RC^{low}$ Tregs with polyclonal stimulation. In one embodiment, the polyclonal stimulation is a stimulation with anti-CD3 mAbs and anti-CD28 mAbs.

The present invention also relates to a population of $CD8^+CD45RC^{low}$ Tregs obtainable or susceptible to be obtained by the method of the invention. The present invention also relates to said population of $CD8^+CD45RC^{low}$ Tregs for use in preventing or reducing transplant or graft rejection or graft versus host disease (GVHD) in a patient in need thereof.

In the present invention, the following terms have the following meanings:

- "About" preceding a figure encompasses plus or minus 10%, or less, of the value of said figure. It is to be understood that the value to which the term "about" refers is itself also specifically, and preferably, disclosed.
- "Allogeneic" or "allogenic" refers to any material (e.g., cells, tissue, organ, graft, transplant) obtained or derived from a different subject of the same specie than the subject to whom/which the material is to be introduced or transplanted. Two or more subjects are said to be allogeneic to one another when the genes at one or more loci are not identical. In some aspects, allogeneic material from subjects of the same species may be sufficiently unlike genetically to interact antigenically.
- "Autologous" refers to any material (e.g., cells, tissue, graft, transplant) obtained or derived from the same subject to whom/which it is later to be re-introduced.
- "Donor" refers to a subject, preferably a human subject, from whom is originating a transplant or a graft.
- "Pharmaceutically acceptable carrier" or "pharmaceutically acceptable excipient" refers to an excipient or carrier that does not produce an adverse, allergic or other untoward reaction when administered to a mammal, preferably a human. It includes any and all solvents, such as, for example, dispersion media, coatings, antibacterial and antifungal agents, isotonic and absorption delaying agents. A pharmaceutically acceptable excipient or carrier refers to a non-toxic solid, semi-solid or liquid filler, diluent, encapsulating material or formulation auxiliary of any type. For human administration, preparations should meet sterility, pyrogenicity, general safety and purity standards as required by the regulatory offices such as the FDA or EMA.
- "Patient" refers to a mammal, preferably a human. In one embodiment of the present invention, a patient is a mammal, preferably a human, requiring a transplant or graft, in particular an allogeneic transplant or graft. Thus, in one embodiment, the patient is a mammal, preferably a human, which/who received, is receiving or is awaiting the receipt of a transplant or a graft. In one embodiment, the patient is a male. In another embodiment, the patient is a female. In one embodiment, the patient is an adult. According to the present invention, an adult is a patient above the age of 18, 19, 20 or 21 years. In another embodiment, the patient is a child. According to the present invention, a child is a patient below 21, 20, 19 or 18 years.
- "Recipient" refers to a patient, preferably a human patient, who received, is receiving or is awaiting the receipt of a transplant or a graft.
- "Therapeutically effective amount" or "therapeutically effective dose" refer to the amount or concentration of an isolated MHC-derived human peptide as defined herein, that is aimed at, without causing significant negative or adverse side effects to the patient in need of treatment, inducing immune tolerance in said patient and/or reducing an immune response, and in particular at preventing or reducing transplant or graft rejection or graft versus host disease (GVHD).
- "Treating" or "treatment" refers to a therapeutic treatment, to a prophylactic or preventative treatment, or to both a therapeutic treatment and a prophylactic or preventative treatment, wherein the object is to induce immune tolerance, that is to say to prevent, slow down (lessen) or reduce an immune response, for example an immune response against a transplant or graft. In one embodiment, the object is to induce tolerance or partial tolerance to a transplant or graft in a patient who received, is receiving or is awaiting the receipt of said transplant or graft. In one embodiment, the object is thus to prevent or reduce transplant or graft rejection. In one embodiment, the object is to prevent or reduce graft versus host disease (GVHD). In one embodiment, a patient is successfully "treated" if, after receiving a therapeutically effective dose of an isolated MHC-derived human peptide as defined herein, the patient shows at least one of the following: a) a decreased level of an immune response, in particular an immune response against a transplant or graft, such as a decreased level of a T cell mediated immune response, a decreased level of a B cell mediated immune response, and/or a decrease level of donor-specific antibodies; b) a delay in the onset or progression of an immune response, in particular an immune response against a transplant or graft; or c) a reduced risk of the onset or progression of an immune response, in particular an immune response against a transplant or graft. The above parameters for assessing successful treatment and improvement in the disease are readily measurable by routine procedures familiar to the physician.
- "Teff" or "Teffs" as used herein refers to an effector T cell or effector T cells, respectively. Teffs are T cells capable of mounting a specific immune response, such as, for example, cytotoxic T cells.
- "Treg" or "Tregs" as used herein refers to a regulatory T cell or regulatory T cells, respectively. Regulatory T cells are a specialized subpopulation of T cells that that suppress an abnormal or excessive immune response and play a role in immune tolerance. The regulatory T cells are typically, but not always, forkhead box P3 ($Foxp3^+$) regulatory T cells and/or $CD45RC^{low}$ regulatory T cells.

BRIEF DESCRIPTION OF THE DRAWINGS

FIG. 1 is a scheme detailing the designed HLA class II peptides (also referred to as MHC class II peptides).

FIG. 2 is a scheme depicting the protocol of $CD8^+$ Tregs activation in presence of the MHC class II peptides.

FIGS. 3A, 3B and 3C show the $CD8^+$ Treg activation in response to human peptides as analyzed by CD25 and CD69 expression. 3A is a graph showing the expression of the activation markers CD25 (black) and CD69 (white) in $CD8^+$ Tregs incubated with the MHC class II peptides. Bars represent the ratio between the percentage of marker positive cells after peptide stimulation and percentage of marker positive cells in the control condition without peptide+/−SEM. *$p<0.05$. n=9 to 14 for each peptide. 3B and 3C are representative histograms of the expression of CD25 (3B) and CD69 (3C) in presence of control peptide, MHC class II peptide (Hpep2) or anti-CD/28 stimulation.

DETAILED DESCRIPTION

Figures 3B, 3C:
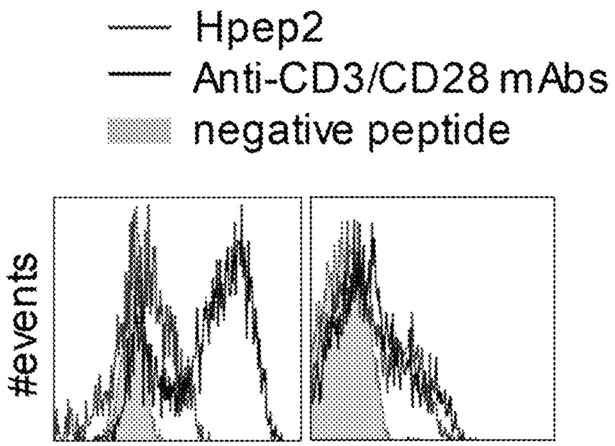

The first object of the present invention relates to an isolated MHC-derived human peptide which comprises a SDVGE-X-R (SEQ ID NO: 13) 7 amino acids motif and which is selected from the group consisting of NQEESVRFDSDVGEFR (Hpep 1—SEQ ID NO:1), NREEYARFDSDVGEFR (Hpep2—SEQ ID NO:2), NREEYVRFDSDVGEYR (Hpep4—SEQ ID NO:4) and any peptide with a length of 16 amino acids comprising the SDVGE-X-R (SEQ ID NO: 13) motif and having an amino acid sequence with at least 80, 85, 86, 87, 88, 90, 91, 92, 93, 94, 95, 96, 97, 98 or 99% identity with SEQ ID NO: 1, SEQ ID NO: 2 or SEQ ID NO: 4.

As used herein, in the motif SDVGE-X-R (SEQ ID NO: 13), X refers to any amino acid, preferably to any of the 20 standard amino acids (A, R, N, D, C, Q, E, G, H, I, L, K, M, F, P, S, T, W, Y and V).

According to one embodiment, the isolated MHC-derived human peptide of the invention as described herein is an isolated donor MHC-derived human peptide or an isolated recipient MHC-derived human peptide. In one embodiment, the isolated MHC-derived human peptide of the invention as described herein is an isolated donor MHC-derived human peptide.

In one embodiment, the isolated MHC-derived human peptide comprising a SDVGE-X-R (SEQ ID NO: 13) 7 amino acids motif is selected from the group consisting of NQEESVRFDSDVGEFR (Hpep 1—SEQ ID NO:1), NREEYARFDSDVGEFR (Hpep2—SEQ ID NO:2), NREEYVRFDSDVGEYR (Hpep4—SEQ ID NO:4) and any peptide having an amino acid sequence as set forth in SEQ ID NO: 1, SEQ ID NO: 2 or SEQ ID NO: 4 with a substitution of two amino acids of SEQ ID NO: 1, SEQ ID NO: 2 or SEQ ID NO: 4, respectively, provided that said substitution is not within the SDVGE-X-R (SEQ ID NO: 13) motif.

In one embodiment, the isolated MHC-derived human peptide comprising a SDVGE-X-R (SEQ ID NO: 13) 7 amino acids motif is selected from the group consisting of NQEESVRFDSDVGEFR (Hpep 1—SEQ ID NO:1), NREEYARFDSDVGEFR (Hpep2—SEQ ID NO:2), NREEYVRFDSDVGEYR (Hpep4—SEQ ID NO:4) and any peptide having an amino acid sequence as set forth in SEQ ID NO: 1, SEQ ID NO: 2 or SEQ ID NO: 4 with a substitution of one amino acid of SEQ ID NO: 1, SEQ ID NO: 2 or SEQ ID NO: 4, respectively, provided that said substitution is not within the SDVGE-X-R (SEQ ID NO: 13) motif.

In one embodiment, the isolated MHC-derived human peptide comprising a SDVGE-X-R (SEQ ID NO: 13) 7 amino acids motif is selected from the group consisting of NQEESVRFDSDVGEFR (Hpep 1—SEQ ID NO:1), NREEYARFDSDVGEFR (Hpep2—SEQ ID NO:2) and NREEYVRFDSDVGEYR (Hpep4—SEQ ID NO:4).

In one embodiment, the isolated MHC-derived human peptide comprising a SDVGE-X-R (SEQ ID NO: 13) 7 amino acids motif is selected from the group consisting of NQEESVRFDSDVGEFR (Hpep 1—SEQ ID NO:1), NREEYARFDSDVGEFR (Hpep2—SEQ ID NO:2) and any peptide with a length of 16 amino acids comprising the SDVGE-X-R (SEQ ID NO: 13) motif and having an amino acid sequence with at least 80, 85, 86, 87, 88, 90, 91, 92, 93, 94, 95, 96, 97, 98 or 99% identity with SEQ ID NO: 1 or SEQ ID NO: 2.

In one embodiment, the isolated MHC-derived human peptide comprising a SDVGE-X-R (SEQ ID NO: 13) 7 amino acids motif is selected from the group consisting of NQEESVRFDSDVGEFR (Hpep 1—SEQ ID NO:1), NREEYVRFDSDVGEYR (Hpep4—SEQ ID NO:4) and any peptide with a length of 16 amino acids comprising the SDVGE-X-R (SEQ ID NO: 13) motif and having an amino acid sequence with at least 80, 85, 86, 87, 88, 90, 91, 92, 93, 94, 95, 96, 97, 98 or 99% identity with SEQ ID NO: 1 or SEQ ID NO: 4.

In one embodiment, the isolated MHC-derived human peptide comprising a SDVGE-X-R (SEQ ID NO: 13) 7 amino acids motif is selected from the group consisting of NREEYARFDSDVGEFR (Hpep2—SEQ ID NO:2), NREEYVRFDSDVGEYR (Hpep4—SEQ ID NO:4) and any peptide with a length of 16 amino acids comprising the SDVGE-X-R (SEQ ID NO: 13) motif and having an amino acid sequence with at least 80, 85, 86, 87, 88, 90, 91, 92, 93, 94, 95, 96, 97, 98 or 99% identity with SEQ ID NO: 2 or SEQ ID NO: 4.

In one embodiment, the isolated MHC-derived human peptide comprising a SDVGE-X-R (SEQ ID NO: 13) 7 amino acids motif is NQEESVRFDSDVGEFR (Hpep 1—SEQ ID NO:1) or a peptide with a length of 16 amino acids comprising the SDVGE-X-R (SEQ ID NO: 13) motif and having an amino acid sequence with at least 80, 85, 86, 87, 88, 90, 91, 92, 93, 94, 95, 96, 97, 98 or 99% identity with SEQ ID NO: 1. In one embodiment, the isolated MHC-derived human peptide comprising a SDVGE-X-R (SEQ ID NO: 13) 7 amino acids motif is NQEESVRFDSDVGEFR (Hpep 1—SEQ ID NO:1) or a peptide having an amino acid sequence as set forth in SEQ ID NO: 1 with a substitution of two amino acids of SEQ ID NO: 1, provided that said substitution is not within the SDVGE-X-R (SEQ ID NO: 13) motif. In one embodiment, the isolated MHC-derived human peptide comprising a SDVGE-X-R (SEQ ID NO: 13) 7 amino acids motif is NQEESVRFDSDVGEFR (Hpep 1—SEQ ID NO:1) or a peptide having an amino acid sequence as set forth in SEQ ID NO: 1 with a substitution of one amino acid of SEQ ID NO: 1, provided that said substitution is not within the SDVGE-X-R (SEQ ID NO: 13) motif. In one embodiment, the isolated MHC-derived human peptide comprising a SDVGE-X-R (SEQ ID NO: 13) 7 amino acids motif is NQEESVRFDSDVGEFR (Hpep 1—SEQ ID NO:1).

In one embodiment, the isolated MHC-derived human peptide comprising a SDVGE-X-R (SEQ ID NO: 13) 7 amino acids motif is NREEYARFDSDVGEFR (Hpep2—SEQ ID NO:2) or a peptide with a length of 16 amino acids comprising the SDVGE-X-R (SEQ ID NO: 13) motif and having an amino acid sequence with at least 80, 85, 86, 87, 88, 90, 91, 92, 93, 94, 95, 96, 97, 98 or 99% identity with SEQ ID NO: 2.

In one embodiment, the isolated MHC-derived human peptide comprising a SDVGE-X-R (SEQ ID NO: 13) 7 amino acids motif is NREEYVRFDSDVGEYR (Hpep4—SEQ ID NO:4) or a peptide with a length of 16 amino acids comprising the SDVGE-X-R (SEQ ID NO: 13) motif and having an amino acid sequence with at least 80, 85, 86, 87, 88, 90, 91, 92, 93, 94, 95, 96, 97, 98 or 99% identity with SEQ ID NO: 4.

By an "isolated" peptide, it is intended that the peptide is essentially free from contaminating cellular components, such as carbohydrate, lipid, or other proteinaceous impurities associated with the polypeptide in nature. Typically, a preparation of isolated peptide contains the peptide in a highly purified form, i.e., at least about 80% pure, at least about 90% pure, at least about 95% pure, or greater than 95% pure, such as 96%, 97%, or 98% or more pure, or greater than 99% pure. One way to show that a particular protein preparation contains an isolated peptide is by the appearance of a single band following SDS-polyacrylamide gel electrophoresis of the protein preparation and Coomassie Brilliant Blue staining of the gel. Alternatively, other analytical chemistry techniques such as high-performance liquid chromatography (HPLC) or mass spectrometry (MS) may also be used to determine purity. A peptide that is the predominant specie present in a preparation is substantially purified.

The term "identity" or "identical", when used in a relationship between the amino acid sequences of two or more polypeptides, refers to the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988). Preferred methods for determining identity are designed to give the largest match between the sequences tested. Methods of determining identity are described in publicly available computer programs. Preferred computer program methods for determining identity between two sequences include the GCG program package, including GAP (Devereux et al., Nucl. Acid. Res. 2, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well-known Smith Waterman algorithm may also be used to determine identity.

According to the invention, the peptide of the present invention may be produced by conventional automated peptide synthesis methods or by recombinant expression. General principles for designing and making proteins are well known to those of skill in the art. For instance, peptides may be synthesized in solution or on a solid support in accordance with conventional techniques. Various automatic synthesizers are commercially available and can be used in accordance with known protocols as described in Stewart and Young; Tam et al., 1983; Merrifield, 1986 and Barany and Merrifield, Gross and Meienhofer, 1979. Peptides of the invention may also be synthesized by solid-phase technology employing an exemplary peptide synthesizer such as a Model 433A from Applied Biosystems Inc. The purity of any given peptide, generated through automated peptide synthesis or through recombinant methods, may be determined using reverse phase HPLC analysis. Chemical authenticity of each peptide may be established by any method well known to those of skill in the art. As an alternative to automated peptide synthesis, recombinant DNA technology may be employed wherein a nucleotide sequence which encodes a peptide of choice is inserted into an expression vector, transformed or transfected into an appropriate host cell and cultivated under conditions suitable for expression herein disclosed below.

A further object of the present invention relates to a nucleic acid molecule that encodes the peptide of the present invention.

In one embodiment, the nucleic acid molecule of the present invention encodes a peptide selected from the group consisting of NQEESVRFDSDVGEFR (Hpep 1—SEQ ID NO:1), NREEYARFDSDVGEFR (Hpep2—SEQ ID NO:2), NREEYVRFDSDVGEYR (Hpep4—SEQ ID NO:4) and any peptide with a length of 16 amino acids comprising the SDVGE-X-R (SEQ ID NO: 13) motif and having an amino acid sequence with at least 80, 85, 86, 87, 88, 90, 91, 92, 93, 94, 95, 96, 97, 98 or 99% identity with SEQ ID NO: 1, SEQ ID NO: 2 or SEQ ID NO: 4.

In one embodiment, the nucleic acid molecule of the present invention encodes the peptide NQEESVRFDSDVGEFR (Hpep 1—SEQ ID NO:1) or a peptide with a length of 16 amino acids comprising the SDVGE-X-R (SEQ ID NO: 13) motif and having an amino acid sequence with at least 80, 85, 86, 87, 88, 90, 91, 92, 93, 94, 95, 96, 97, 98 or 99% identity with SEQ ID NO: 1. In one embodiment, the nucleic acid molecule of the present invention encodes the peptide NQEESVRFDSDVGEFR (Hpep 1—SEQ ID NO:1) or a peptide having an amino acid sequence as set forth in SEQ ID NO: 1 with a substitution of one or two amino acid(s) of SEQ ID NO: 1, provided that said substitution is not within the SDVGE-X-R (SEQ ID NO: 13) motif.

As used herein, the term “nucleic acid molecule” has its general meaning in the art and refers to a DNA or RNA molecule. However, the term captures sequences that include any of the known base analogues of DNA and RNA such as, but not limited to 4-acetylcytosine, 8-hydroxy-N6-methyladenosine, aziridinylcytosine, pseudoisocytosine, 5-(carboxyhydroxylmethyl) uracil, 5-fiuorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, -uracil-5-oxyacetic acid methylester, uracil-5-oxyacetic acid, pseudouracil, queosine, 2-thiocytosine, and 2,6-diaminopurine.

In one embodiment, the nucleic acid molecule of the present invention is a viral genome comprising a nucleic acid sequence encoding the peptide as described hereinabove. In one embodiment, the nucleic acid molecule of the present invention is a recombinant viral genome comprising a nucleic acid sequence encoding the peptide as described hereinabove.

A further object of the present invention relates to a vector comprising the nucleic acid molecule as described hereinabove.

Examples of vectors include, without being limited to, plasmids, phagemids, viruses, in particular recombinant viruses.

In one embodiment, the vector of the invention is a virus, in particular a recombinant virus. Thus, the present invention also relates to a virus, in particular a recombinant virus, comprising a nucleic acid molecule encoding the peptide as described hereinabove.

Examples of viruses include, without being limited to, adenoviruses, adeno-associated viruses, lentiviruses, retroviruses.

According to one embodiment, the peptide of the present invention is fused or conjugated to an antibody thus forming an “immunoconjugate”.

Typically, the antibody, to which the peptide of the present invention is fused or conjugated, is directed against a surface antigen of an antigen presenting cell (APC) so that the peptide of the present invention is targeted to said cell to elicit an immune response (e.g., tolerance). As used herein the term “antigen presenting cells” (APC) refers to cells that are capable of activating T-cells, and include, but are not limited to, certain macrophages, B cells and dendritic cells.

In some embodiments, the antibody is directed against a surface antigen of a dendritic cell. “Dendritic cells” (DCs) refer to any member of a diverse population of morphologically similar cell types found in lymphoid or non-lymphoid tissues. These cells are characterized by their distinctive morphology, high levels of surface MHC-class II expression (Steinman, et al., Ann. Rev. Immunol. 9:271 (1991); incorporated herein by reference for its description of such cells). These cells can be isolated from a number of tissue sources, and conveniently, from peripheral blood, herein disclosed.

Accordingly, in one embodiment, the antibody is selected from an antibody that specifically binds to dendritic cell immunoreceptor (DCIR), MHC class I, MHC class II, CD1, CD2, CD3, CD4, CD8, CDl lb, CD14, CD15, CD16, CD19, CD20, CD29, CD31, CD40, CD43, CD44, CD45, CD54, CD56, CD57, CD58, CD83, CD86, CMRF-44, CMRF-56, DCIR, DC-ASPGR, CLEC-6, CD40, BDCA-2, MARCO, DEC-205, mannose receptor, Langerin, DECTIN-1, B7-1, B7-2, IFN-γ receptor and IL-2 receptor, ICAM-1, Fey receptor, LOX-1, and/or ASPGR.

In some embodiments, the antibody is specific for a cell surface marker of a professional antigen presenting cell (APC), in particular a professional APC selected from dendritic cells (DCs), macrophages and B cells.

In one embodiment, the antibody is specific for a cell surface marker of a dendritic cell, for example, CD83, CMRF-44 or CMRF-56.

In one embodiment, the antibody may be specific for a cell surface marker of another professional antigen presenting cell, such as a B cell or a macrophage. For example, CD40 is expressed on dendritic cells, B cells, and other antigen presenting cells so that a larger number of antigen presenting cells would be recruited. In one embodiment, the antibody is specific for CD40.

Techniques for conjugating molecule to antibodies are well-known in the art (See, e.g., Amon et al., “Monoclonal Antibodies For Immunotargeting Of Drugs In Cancer Therapy,” in Monoclonal Antibodies And Cancer Therapy (Reisfeld et al. eds., Alan R. Liss, Inc., 1985); Hellstrom et al., “Antibodies For Drug Delivery,” in Controlled Drug Delivery (Robinson et al. eds., Marcel Deiker, Inc., 2nd ed. 1987); Thorpe, “Antibody Carriers Of Cytotoxic Agents In Cancer Therapy: A Review,” in Monoclonal Antibodies ’84: Biological And Clinical Applications (Pinchera et al. eds., 1985); “Analysis, Results, and Future Prospective of the Therapeutic Use of Radiolabeled Antibody In Cancer Therapy,” in Monoclonal Antibodies For Cancer Detection And Therapy (Baldwin et al. eds., Academic Press, 1985); and Thorpe et al., 1982, Immunol. Rev. 62:119-58. See also, e.g., PCT publication WO 89/12624.) Typically, the nucleic acid molecule is covalently attached to lysines or cysteines on the antibody, through N-hydroxysuccinimide ester or maleimide functionality respectively. Methods of conjugation using engineered cysteines or incorporation of unnatural amino acids have been reported to improve the homogeneity of the conjugate (Axup, J. Y., Bajjuri, K. M., Ritland, M., Hutchins, B. M., Kim, C. H., Kazane, S. A., Halder, R., Forsyth, J. S., Santidrian, A. F., Stafin, K., et al. (2012). Synthesis of site-specific antibody-drug conjugates using unnatural amino acids. Proc. Natl. Acad. Sci. USA 109, 16101-16106.; Junutula, J. R., Flagella, K. M., Graham, R. A., Parsons, K. L., Ha, E., Raab, H., Bhakta, S., Nguyen, T., Dugger, D. L., Li, G., et al. (2010). Engineered thio-trastuzumab-DM1 conjugate with an improved therapeutic index to target human epidermal growth factor receptor 2-positive breast cancer. Clin. Cancer Res.16, 4769-4778.). Junutula et al. (2008) developed cysteine-based site-specific conjugation called "THIOMABs" (TDCs) that are claimed to display an improved therapeutic index as compared to conventional conjugation methods. Conjugation to unnatural amino acids that have been incorporated into the antibody is also being explored for antibody-drug conjugates (ADCs); however, the generality of this approach is yet to be established (Axup et al., 2012). In particular the one skilled in the art can also envisage Fc-containing polypeptide engineered with an acyl donor glutamine-containing tag (e.g., Gin-containing peptide tags or Q-tags) or an endogenous glutamine that are made reactive by polypeptide engineering (e.g., via amino acid deletion, insertion, substitution, or mutation on the polypeptide). Then a transglutaminase, can covalently crosslink with an amine donor agent (e.g., a small molecule comprising or attached to a reactive amine) to form a stable and homogenous population of an engineered Fc-containing polypeptide conjugate with the amine donor agent being site-specifically conjugated to the Fc-containing polypeptide through the acyl donor glutamine-containing tag or the accessible/exposed/reactive endogenous glutamine (WO2012/059882).

A further object of the present invention relates to a nanoparticle that comprises a least one peptide of the present invention.

In one embodiment, the nanoparticle of the present invention comprises a peptide selected from the group consisting of NQEESVRFDSDVGEFR (Hpep 1—SEQ ID NO:1), NREEYARFDSDVGEFR (Hpep2—SEQ ID NO:2), NREEYVRFDSDVGEYR (Hpep4—SEQ ID NO:4) and any peptide with a length of 16 amino acids comprising the SDVGE-X-R (SEQ ID NO: 13) motif and having an amino acid sequence with at least 80, 85, 86, 87, 88, 90, 91, 92, 93, 94, 95, 96, 97, 98 or 99% identity with SEQ ID NO: 1, SEQ ID NO: 2 or SEQ ID NO: 4.

In one embodiment, the nanoparticle of the present invention comprises the peptide NQEESVRFDSDVGEFR (Hpep 1—SEQ ID NO:1) or a peptide with a length of 16 amino acids comprising the SDVGE-X-R (SEQ ID NO: 13) motif and having an amino acid sequence with at least 80, 85, 86, 87, 88, 90, 91, 92, 93, 94, 95, 96, 97, 98 or 99% identity with SEQ ID NO: 1. In one embodiment, the nanoparticle of the present invention comprises the peptide NQEESVRFDSDVGEFR (Hpep 1—SEQ ID NO:1) or a peptide having an amino acid sequence as set forth in SEQ ID NO: 1 with a substitution of one or two amino acid(s) of SEQ ID NO: 1, provided that said substitution is not within the SDVGE-X-R (SEQ ID NO: 13) motif.

As used herein, the term "nanoparticles" means particles from about 1 nm to about 1000 nm, preferably from about 2 to about 500 nm and even more preferably from about 5 to about 300 nm in size. For most nanoparticles, the size of the nanoparticles is the distance between the two most distant points in the nanoparticle. For anisotropic nanoparticles, such as tubes whiskers or cylinders, the size of the diameter is the diameter of the smallest cylinder in which the nanoparticle is inscribed. Nanoparticle size can be determined by different methods such as Dynamic Light Scattering (DLS), Small Angle X-ray Scattering (SAXS), Scanning Mobility Particle Sizer (SMPS), Scanning Electron Microscopy (SEM), Transmission Electron Microscopy (TEM) (Orts-Gil, G., K. Natte, et al. (2011), Journal of Nanoparticle Research 13(4): 1593-1604; Alexandridis, P. and B. Lindman (2000), Amphiphilic Block Copolymers: Self-Assembly and Applications, Elsevier Science; Hunter, R. J. and L. R. White (1987). Foundations of colloid science, Clarendon Press.). The nanoparticles may be made of different chemical nature, of different sizes, and/or of different shapes. The nanoparticles can be in the form of a sphere, needle, flake, platelet, tube, fiber, cube, prism, whiskers or have an irregular shape.

In some embodiments, the nanoparticles are selected among solid nanoparticles. In some embodiments, nanoparticles can be inorganic, organic or mixed.

In one embodiment, the nanoparticle is a mineral nanoparticle. Among the mineral nanoparticles, one can mention metal oxides, alumina, silica, kaolin, hydroxyapatite, calcium carbonate, silicates such as micas quartz, zeolites or clays such as hectorite, laponite, montmorillonite, bentonite, smectite . . . . Mineral particles may include, but are not limited to, metal particles. In one embodiment, the nanoparticle is a metal nanoparticle. Metal particles encompass particles formed exclusively with metallic alloys or metals chosen among alkaline earth metal, transitional metal, rare earth metal, and alloys thereof. In some embodiments, the metal may be aluminum, copper, cadmium, selenium, silver, gold, indium, iron, platinum, nickel, molybdenum, silicon, titanium, tungsten, antimony, palladium, zinc, tin, and alloys thereof. In one embodiment, these metal particles may be metal organo modified nanoparticles having chemical entities grafted to their surface or having a self-assembled monolayer of compounds, such as organosulfur compounds, on their surface. In some embodiments, the nanoparticles may be nanoparticles of metal oxides, such as iron oxides (FeO, Fe2O3, Fe3O4), cerium oxide (CeO), alumina (Al2O3), zirconium oxide (ZrO2), titanium oxide (TiO2), titanates (BaTiO3, Ba0.5Sr0.5TiO3, SrTiO3), indium oxide (In2O3), tin oxide (SnO2), antimony oxide (Sb2O3), magnesium oxide (MgO), calcium oxide (CaO), manganese oxides (Mn3O4, MnO2), molybdenum oxide (MoO3), silica (SiO2), zinc oxide (ZnO), yttrium oxide (Y2O3), bismuth oxychloride, copper oxides (CuO, Cu2O). In one embodiment, the nanoparticles can also be organo-metallic nanoparticles: they are metal or metal oxide, carbides, nitrides, borides, sulphides and hydroxides nanoparticles, coated or grafted by an organic material. In one embodiment, the nanoparticles can be selected among metal inorganic salts: inorganic salts include barium sulfate, calcium carbonate, calcium sulfate, calcium phosphate, magnesium hydrogen carbonate (including sugar moieties).

In one embodiment, the nanoparticle is organic. When the nanoparticle is organic, it is usually an organic polymer. Organic polymers encompass, but are not limited to, polystyrene, poly(vinyl acetate), poly(methylstyrene), poly(acrylamide), poly(acrylonitrile), poly(vinyl chloride), poly(butyl acrylate), poly(acrylic acid), copolymers of styrene and C1-C4alkyl (meth)acrylate, copolymers of styrene and acrylamide, copolymers of styrene and acrylonitrile, copolymers of styrene and vinyl acetate, copolymers of acrylamide and C1-C4 alkyl (meth)acrylates, copolymers from acrylonitrile and C1-C4 alkyl (meth)acrylate, copolymers of acrylonitrile and acrylamide, terpolymers from styrene, acrylonitrile and acrylamide, poly(methyl methacrylate), poly(ethyl methacrylate), copolymers styrene/butadiene, styrene/acrylic acid, styrene/vinylpyrrolidone and butadiene/acrylonitrile, or methoxy poly(ethylene glycol)-poly(lactide) copolymer (MPEG-PLA). Polymer particles can be crosslinked or not. For instance, organic particles include, but are not limited to, nylon (for example marketed by ATOCHEM), polyethylene powders (for example marketed by PLAST LABOR), poly-2-alanine powders, polyfluorinated powders such as poly-tetrafluoroethylene (for example marketed by DUPONT DE NEMOURS), acrylic copolymer powders (for example marketed by DOW CHEMICA), polystyrene powders (for example marketed by PRESPERESE), polyester powders, expanded microspheres in thermoplastic material (for example marketed by EXPANCEL), microballs of silicon resins (for example marketed by TOSHIBA), synthetic hydrophilic polymer powders such as polyacrylates (for example marketed by MATSUMOTO), acrylic polyamides (for example marketed by ORIS), insoluble polyurethanes (for example marketed by TOSHNU), porous microspheres of cellulose, micro- or nanoparticles of PTFE (polytetrafluoroethylene).

In some embodiment, the nanoparticles are made of polysaccharides, i.e., molecules comprising two or more monosaccharide units. Typically, the polysaccharide is selected from the group consisting of dextran, pullulan, agar, alginic acid, hyaluronic acid, inulin, heparin, fucoidan, chitosan and mixtures thereof. In a particular embodiment, the polysaccharide is a mixture of pullulan/dextran.

In some embodiments, the nanoparticles are inorganic. In one embodiment, the nanoparticles are selected from: clays, silicates, alumina, silica, kaolin, carbon nanotubes cellulose nanocrystals, hydroxyapatite, magnetic nanoparticles like iron oxides, calcium carbonates, and core-shell particles such as iron oxide core/silica shell particles. In one embodiment, small molecules or polymer chains can be grafted to stabilize nanoparticles in suspensions when necessary. In some embodiments, at least one part of the nanoparticles are silica nanoparticles.

Typically, the peptide of the present invention is preferably covalently linked to the nanoparticle, e.g., by carbodiimide or succinimide coupling or by another method of covalently coupling peptides. In one embodiment, the peptide of the present invention is localized on the outside of the nanoparticle. The peptide may also be non-covalently associated to the nanoparticle.

As used herein, the term “nanoparticle” encompasses liposomes, polymer micelles, polymer-DNA complexes (polycomplexes), nanospheres, nanofibres, nanotubes, and nanocapsules. All these nanoparticles are known in the art. The surface of such nanoparticles is often modified by PEG brush (PEGylation, i.e., polyethylene glycol (PEG) is attached to the surface of the nanoparticles).

In some embodiments, the nanoparticle is a nanocapsule. As used herein, the term “nanocapsules” refers to vesicular systems in which the drug, i.e., the peptide of the present invention, is confined to a cavity surrounded by a unique polymer membrane.

In some embodiments, the nanoparticle is a nanosphere. As used herein, the term “nanosphere” refers to a matrix system in which the drug, i.e., the peptide of the present invention, is physically and uniformly dispersed.

In some embodiments, the nanoparticle is a liposome.

Thus, a further object of the present invention relates to a liposome that comprises a least one peptide as described hereinabove.

In one embodiment, the liposome of the present invention comprises a peptide selected from the group consisting of NQEESVRFDSDVGEFR (Hpep 1—SEQ ID NO:1), NREEYARFDSDVGEFR (Hpep2—SEQ ID NO:2), NREEYVRFDSDVGEYR (Hpep4—SEQ ID NO:4) and any peptide with a length of 16 amino acids comprising the SDVGE-X-R (SEQ ID NO: 13) motif and having an amino acid sequence with at least 80, 85, 86, 87, 88, 90, 91, 92, 93, 94, 95, 96, 97, 98 or 99% identity with SEQ ID NO: 1, SEQ ID NO: 2 or SEQ ID NO: 4.

In one embodiment, the liposome of the present invention comprises the peptide NQEESVRFDSDVGEFR (Hpep 1—SEQ ID NO:1) or a peptide with a length of 16 amino acids comprising the SDVGE-X-R (SEQ ID NO: 13) motif and having an amino acid sequence with at least 80, 85, 86, 87, 88, 90, 91, 92, 93, 94, 95, 96, 97, 98 or 99% identity with SEQ ID NO: 1. In one embodiment, the liposome of the present invention comprises the peptide NQEESVRFDSDVGEFR (Hpep 1—SEQ ID NO:1) or a peptide having an amino acid sequence as set forth in SEQ ID NO: 1 with a substitution of one or two amino acid(s) of SEQ ID NO: 1, provided that said substitution is not within the SDVGE-X-R (SEQ ID NO: 13) motif.

As used herein, the term “liposome” refers to any structure composed of a lipid bilayer that enclose one or more volumes, wherein the volume can be an aqueous compartment. Liposome consist of one, two, three, four, five, six, seven, eight, nine, ten or more lipid bilayers. The term “lipid bilayer” includes, but is not limited to: phospholipid bilayer, bilayer consisting of nonionic surfactants. Liposomes consisting of a phospholipid bilayer can be composed of naturally-derived phospholipids with mixed lipid chains (e.g., phosphatidylethanolamine), or of pure components like DOPE (dioleolylphosphatidyl-ethanolamine) but are not limited to these components. Liposomes include—but are not limited to—emulsions, foams, micelles, exosomes, vesicles, insoluble monolayers, liquid crystals, phospholipid dispersions, lamellar layers and the like. The term “liposome” also includes so called “stealth liposomes” which consist of water-soluble polymers (e.g., polyethylene glycol (PEG)) attached to the surface of conventional liposomes composed of a lipid mono- or bilayer that enclose a volume (e.g., so called PEGylated liposomes). A wide variety of methods for preparing liposomes suitable for targeting to the blood-brain barrier in the present invention is available. See, for example, Szoka et al., Ann. Rev. Biophys. Bioeng. 9:467 (1980), Liposome Technology, ed. G. Gregoriadis, CRC Press, Inc., Boca Raton, Fla. (1984), U.S. Pat. Nos. 4,235,871, 4,501,728, 4,837,028, 4,957,735 and 5,019,369, each of which is incorporated herein by reference. Following liposome preparation, the liposomes may be sized to achieve a desired size range and relatively narrow distribution of liposome sizes.

Methods of coupling peptides according to the present invention to liposomes generally involve covalent cross linking between a liposomal lipid and a peptide. In another approach, a peptide according to the present invention has been covalently derivatized with a hydrophobic anchor, such as fatty acids, is incorporated into a preformed lipid.

The peptide, the immunoconjugate and the nanoparticle herein disclosed may be administered as part of one or more pharmaceutical compositions. Accordingly, one object of the present invention relates to a pharmaceutical composition comprising a peptide as described hereinabove, an immunoconjugate as described hereinabove or a nanoparticle as described hereinabove and at least one pharmaceutically acceptable carrier.

In one embodiment, the pharmaceutical composition of the present invention comprises the peptide NQEESVRFDSDVGEFR (Hpep 1—SEQ ID NO:1) or a peptide with a length of 16 amino acids comprising the SDVGE-X-R (SEQ ID NO: 13) motif and having an amino acid sequence with at least 80, 85, 86, 87, 88, 90, 91, 92, 93, 94, 95, 96, 97, 98 or 99% identity with SEQ ID NO: 1 and at least one pharmaceutically acceptable carrier. In one embodiment, the pharmaceutical composition of the present invention comprises the peptide NQEESVRFDSDVGEFR (Hpep 1—SEQ ID NO:1) or a peptide having an amino acid sequence as set forth in SEQ ID NO: 1 with a substitution of one or two amino acid(s) of SEQ ID NO: 1, provided that said substitution is not within the SDVGE-X-R (SEQ ID NO: 13) motif and at least one pharmaceutically acceptable carrier.

The term "pharmaceutical composition" refers to a composition as described herein, in particular a composition comprising a peptide according to the present invention, an immunoconjugate according to the present invention or a nanoparticle according to the present invention, or pharmaceutically acceptable salt thereof, with other agents such as carriers and/or excipients. The pharmaceutical compositions as provided herein typically include a pharmaceutically acceptable carrier. The term "pharmaceutically acceptable carrier" includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical-Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the peptides of the present invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogen free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In particular, the peptide, the immunoconjugate and the nanoparticle herein disclosed are particularly suitable for preparing vaccine composition. Accordingly, one object of the present invention relates to a vaccine composition comprising a peptide as described hereinabove, an immunoconjugate as described hereinabove or a nanoparticle as described hereinabove and at least one pharmaceutically acceptable carrier.

In one embodiment, the vaccine composition of the present invention comprises the peptide NQEESVRFDSDVGEFR (Hpep 1—SEQ ID NO:1) or a peptide with a length of 16 amino acids comprising the SDVGE-X-R (SEQ ID NO: 13) motif and having an amino acid sequence with at least 80, 85, 86, 87, 88, 90, 91, 92, 93, 94, 95, 96, 97, 98 or 99% identity with SEQ ID NO: 1 and at least one pharmaceutically acceptable carrier. In one embodiment, the vaccine composition of the present invention comprises the peptide NQEESVRFDSDVGEFR (Hpep 1—SEQ ID NO:1) or a peptide having an amino acid sequence as set forth in SEQ ID NO: 1 with a substitution of one or two amino acid(s) of SEQ ID NO: 1, provided that said substitution is not within the SDVGE-X-R (SEQ ID NO: 13) motif and at least one pharmaceutically acceptable carrier.

For the purpose of the present invention, the term "vaccine composition" refers to a composition which can be administered to humans or to animals in order to induce an immune response; this immune response can result in the activation of certain cells, in particular antigen-presenting cells, T lymphocytes including Tregs, and B lymphocytes.

Accordingly, in some embodiments, the vaccine composition of the present invention comprises an adjuvant. In one embodiment, the term "adjuvant" refers to a compound that lacks significant activity administered alone but can potentiate the activity of another therapeutic agent. In some embodiments, the adjuvant is Incomplete Freund's adjuvant (IFA) or other oil-based adjuvant. In one embodiment, the adjuvant is present between 30-70%, preferably between 40-60%, more preferably between 45-55% proportion weight by weight (w/w).

In some embodiments, the vaccine composition of the present invention comprises at least one Toll-Like Receptor (TLR) agonist which is selected from the group consisting of TLR1, TLR2, TLR3, TLR4, TLR5, TLR6, TLR7, and TLR8 agonists.

The pharmaceutical composition and the vaccine composition of the present invention can be delivered to a patient using a wide variety of routes or modes of administration. Suitable routes of administration include, but are not limited to, inhalation, transdermal, oral, rectal, transmucosal, intestinal and parenteral administration, including intramuscular, subcutaneous and intravenous injections.

A further object of the invention is a peptide as described hereinabove, a nanoparticle as described hereinabove, an immunoconjugate as described hereinabove, a pharmaceutical composition as described hereinabove or a vaccine composition as described hereinabove for use as a medicament.

In one embodiment, the present invention relates to the peptide NQEESVRFDSDVGEFR (Hpep 1—SEQ ID NO:1) or a peptide with a length of 16 amino acids comprising the SDVGE-X-R (SEQ ID NO: 13) motif and having an amino acid sequence with at least 80, 85, 86, 87, 88, 90, 91, 92, 93, 94, 95, 96, 97, 98 or 99% identity with SEQ ID NO: 1 for use as a medicament. In one embodiment, the present invention relates to the peptide NQEESVRFDSDVGEFR (Hpep 1—SEQ ID NO:1) or a peptide having an amino acid sequence as set forth in SEQ ID NO: 1 with a substitution of one or two amino acid(s) of SEQ ID NO: 1, provided that said substitution is not within the SDVGE-X-R (SEQ ID NO: 13) motif, for use as a medicament.

The peptide, nanoparticle, immunoconjugate, pharmaceutical composition or vaccine composition of the present invention is particularly suitable for inducing immune tolerance. Accordingly, one object of the invention relates to a peptide as described hereinabove, a nanoparticle as described hereinabove, an immunoconjugate as described hereinabove, a pharmaceutical composition as described hereinabove or a vaccine composition as described hereinabove for use in inducing immune tolerance.

In one embodiment, the present inventions relates to the peptide NQEESVRFDSDVGEFR (Hpep 1—SEQ ID NO:1) or a peptide with a length of 16 amino acids comprising the SDVGE-X-R (SEQ ID NO: 13) motif and having an amino acid sequence with at least 80, 85, 86, 87, 88, 90, 91, 92, 93, 94, 95, 96, 97, 98 or 99% identity with SEQ ID NO: 1 for use in inducing immune tolerance. In one embodiment, the present invention relates to the peptide NQEESVRFDSDVGEFR (Hpep 1—SEQ ID NO:1) or a peptide having an amino acid sequence as set forth in SEQ ID NO: 1 with a substitution of one or two amino acid(s) of SEQ ID NO: 1, provided that said substitution is not within the SDVGE-X-R (SEQ ID NO: 13) motif, for use in inducing immune tolerance.

As used herein, the term "immune tolerance" refers to a state of unresponsiveness of the immune system to substances or tissues that have the capacity to elicit an immune response.

Thus, in one embodiment, the peptide as described hereinabove, the nanoparticle as described hereinabove, the immunoconjugate as described hereinabove, the pharmaceutical composition as described hereinabove or the vaccine composition as described hereinabove is for use in reducing an immune response. In one embodiment, the present inventions relates to the peptide NQEESVRFDSDVGEFR (Hpep 1—SEQ ID NO:1) or a peptide with a length of 16 amino acids comprising the SDVGE-X-R (SEQ ID NO: 13) motif and having an amino acid sequence with at least 80, 85, 86, 87, 88, 90, 91, 92, 93, 94, 95, 96, 97, 98 or 99% identity with SEQ ID NO: 1 for use in reducing an immune response. In one embodiment, the present invention relates to the peptide NQEESVRFDSDVGEFR (Hpep 1—SEQ ID NO:1) or a peptide having an amino acid sequence as set forth in SEQ ID NO: 1 with a substitution of one or two amino acid(s) of SEQ ID NO: 1, provided that said substitution is not within the SDVGE-X-R (SEQ ID NO: 13) motif, for use in reducing an immune response.

Peptides of the invention are useful for achieving tolerance or partial tolerance against the transplant upon transplantation of said transplant. As used herein, a "partial tolerance" is a partial immune tolerance which results in a reduced immune response. As used herein, the term "immune response" includes T cell mediated and/or B cell mediated immune responses. Exemplary immune responses include T cell responses, e.g., cytokine production and cellular cytotoxicity, in addition, the term immune response includes immune responses that are indirectly effected by T cell activation, e.g., antibody production (humoral responses) and activation of cytokine responsive cells, e.g., macrophages. Immune cells involved in the immune response include lymphocytes, such as B cells and T cells (CD4+, CD8+, Th1 and Th2 cells); antigen presenting cells (e.g., professional antigen presenting cells such as dendritic cells); natural killer cells; myeloid cells, such as macrophages, eosinophils, mast cells, basophils, and granulocytes. For instance, immune responses are involved in transplant rejection, as well as in the concomitant physiological result of such immune responses, such as for example, interstitial fibrosis, chronic graft arteriosclerosis, or vasculitis.

In one embodiment, said immune tolerance is a tolerance or a partial tolerance of a patient to a transplant or graft upon transplantation of said transplant or graft in the patient. In other words, in one embodiment, said immune tolerance is a tolerance or a partial tolerance to a transplant or graft in a patient who received, is receiving or is awaiting the receipt of said transplant or a graft. Thus, in one embodiment, the immune tolerance is a reduction of an immune response of a patient, in particular of an immune response against a transplant or graft of a patient who received, is receiving or is awaiting the receipt of said transplant or a graft. In one embodiment, said immune tolerance is a donor-specific or recipient-specific immune tolerance.

In one embodiment, said immune tolerance is a donor-specific immune tolerance. As used herein "donor-specific immune tolerance" refers to an immune tolerance to a transplant or graft from a donor with a major histocompatibility complex (MHC, e.g., MHC class I and/or MHC class II) haplotype which contains the peptide as described herein, in particular the peptide NQEESVRFDSDVGEFR (Hpep 1—SEQ ID NO:1) or a peptide with a length of 16 amino acids comprising the SDVGE-X-R (SEQ ID NO: 13) motif and having an amino acid sequence with at least 80, 85, 86, 87, 88, 90, 91, 92, 93, 94, 95, 96, 97, 98 or 99% identity with SEQ ID NO: 1. In one embodiment, "donor-specific immune tolerance" refers to an immune tolerance to a transplant or graft from a donor with a MHC class II haplotype which contains the peptide as described herein, in particular the peptide NQEESVRFDSDVGEFR (Hpep 1—SEQ ID NO:1) or a peptide with a length of 16 amino acids comprising the SDVGE-X-R (SEQ ID NO: 13) motif and having an amino acid sequence with at least 80, 85, 86, 87, 88, 90, 91, 92, 93, 94, 95, 96, 97, 98 or 99% identity with SEQ ID NO: 1.

In one embodiment, said immune tolerance is a recipient-specific immune tolerance. As used herein "recipient-specific immune tolerance" refers to an immune tolerance induced in a transplant or graft from a donor towards a recipient, said recipient having a major histocompatibility complex (MHC, e.g., MHC class I and/or MHC class II) haplotype which contains the peptide as described herein, in particular the peptide NQEESVRFDSDVGEFR (Hpep 1—SEQ ID NO:1) or a peptide with a length of 16 amino acids comprising the SDVGE-X-R (SEQ ID NO: 13) motif and having an amino acid sequence with at least 80, 85, 86, 87, 88, 90, 91, 92, 93, 94, 95, 96, 97, 98 or 99% identity with SEQ ID NO: 1. In one embodiment, "recipient-specific immune tolerance" refers to an immune tolerance induced in a transplant or graft from a donor towards a recipient, said recipient having a MHC class II haplotype which contains the peptide as described herein, in particular the peptide NQEESVRFDSDVGEFR (Hpep 1—SEQ ID NO:1) or a peptide with a length of 16 amino acids comprising the SDVGE-X-R (SEQ ID NO: 13) motif and having an amino acid sequence with at least 80, 85, 86, 87, 88, 90, 91, 92, 93, 94, 95, 96, 97, 98 or 99% identity with SEQ ID NO: 1.

Thus, in one embodiment, the patients treated with a peptide, immunoconjugate, nanoparticle, pharmaceutical composition, or vaccine composition of the present invention, in particular in comparison with untreated patients, display at least one of the following physiological features: a) a decreased level of an immune response against the transplant (that may be mediated at least in part by B cell mediated immune responses, more particularly donor-specific antibodies); b) a delay in the onset or progression of an immune response against the transplant; or c) a reduced risk of the onset or progression of an immune response against the transplant.

Accordingly, the peptide, immunoconjugate, nanoparticle, pharmaceutical composition or vaccine composition of the present invention is particularly suitable in a method of preventing or reducing transplant or graft rejection in a patient in need thereof.

In one embodiment, the peptide, immunoconjugate or pharmaceutical composition of the present invention is particularly suitable in a method of preventing or reducing graft versus host disease (GVHD).

In one embodiment, the GVHD follows the transplantation or graft of cells, preferably multipotent hematopoietic stem cells, in particular multipotent hematopoietic stem cells derived from the bone marrow or peripheral blood of a donor.

Thus, one object of the invention relates to a peptide as described hereinabove, an immunoconjugate as described hereinabove, a nanoparticle as described hereinabove, a pharmaceutical composition as described hereinabove or a vaccine composition as described hereinabove for use in preventing or reducing transplant or graft rejection or graft versus host disease (GVHD) in a patient in need thereof.

The present invention also relates to a method for preventing or reducing transplant or graft rejection or graft versus host disease (GVHD) in a patient in need thereof, comprising administering to said patient a peptide as described hereinabove, an immunoconjugate as described hereinabove, a nanoparticle as described hereinabove, a pharmaceutical composition as described hereinabove or a vaccine composition as described hereinabove.

The present invention also relates to the use of a peptide as described hereinabove, an immunoconjugate as described hereinabove, a nanoparticle as described hereinabove, a pharmaceutical composition as described hereinabove or a vaccine composition as described hereinabove for the manufacture of a medicament for preventing or reducing transplant or graft rejection or graft versus host disease (GVHD) in a patient in need thereof.

As mentioned above, in one embodiment, the peptide is NQEESVRFDSDVGEFR (Hpep 1—SEQ ID NO:1) or a peptide with a length of 16 amino acids comprising the SDVGE-X-R (SEQ ID NO: 13) motif and having an amino acid sequence with at least 80, 85, 86, 87, 88, 90, 91, 92, 93, 94, 95, 96, 97, 98 or 99% identity with SEQ ID NO: 1. In one embodiment, the peptide is NQEESVRFDSDVGEFR (Hpep 1—SEQ ID NO:1) or a peptide having an amino acid sequence as set forth in SEQ ID NO: 1 with a substitution of one or two amino acid(s) of SEQ ID NO: 1, provided that said substitution is not within the SDVGE-X-R (SEQ ID NO: 13) motif.

As used herein, the terms “transplant” and “graft” refer to any material from a donor subject (e.g., cells, tissue, organ or fragment thereof) that is inserted or to be inserted in a recipient subject, i.e., in a patient in need thereof. In one embodiment, the transplant or graft is an organ, a tissue or cells. More particularly, as used herein “transplant” preferably refers to material from a donor subject consisting of a tissue or an organ or a fragment thereof. More particularly, as used herein “graft” preferably refers to material from a donor subject consisting of cells.

In one embodiment, the transplant or graft consists in cells that are selected from the group comprising or consisting of multipotent hematopoietic stem cells derived from bone marrow, peripheral blood, or umbilical cord blood; and pluripotent (i.e., embryonic stem cells (ES) or induced pluripotent stem cells (iPS)) or multipotent stem cell-derived differentiated cells of different cell lineages such as cardiomyocytes, beta-pancreatic cells, hepatocytes, neurons. In one embodiment, the transplant or graft consisting in cells is used for hematopoietic stem cell transplantation (HSCT) and thus comprises multipotent hematopoietic stem cells, usually derived from bone marrow, peripheral blood, or umbilical cord blood. HSCT may be curative for patients suffering from a leukemia or a lymphoma. However, an important limitation of HSCT, in particular allogeneic HSCT, is the development of graft versus host disease (GVHD), which occurs in a severe form in about 30-50% of patients who receive this therapy.

In one embodiment, the patient in need thereof is affected with a disease selected from the group comprising or consisting of acute myeloid leukemia (AML); acute lymphoid leukemia (ALL); chronic myeloid leukemia (CML); myelodysplasia syndrome (MDS)/myeloproliferative syndrome; lymphomas such as Hodgkin and non-Hodgkin lymphomas, chronic lymphatic leukemia (CLL) and multiple myeloma.

In one embodiment, the patient in need thereof received, is receiving or is awaiting the receipt of a transplant or graft consisting in cells, preferably in multipotent hematopoietic stem cells, in particular in multipotent hematopoietic stem cells derived from the bone marrow or peripheral blood of a donor.

In one embodiment, the transplant or graft is syngeneic, that is to say the donor subject and the recipient subject are genetically identical. In one embodiment, the transplant or graft is allogeneic, that is to say the donor subject and the recipient subject are of different genetic origins but of the same species. In one embodiment, the transplant or graft is xenogeneic, that is to say the donor subject and the recipient subject are from different species.

In one embodiment, the transplant or graft is from a human donor. The human donor of the transplant can be a living donor or a deceased donor, namely a cadaveric donor.

In one embodiment, the transplant or graft is from a human donor with a major histocompatibility complex (MHC, e.g., MHC class I and/or MHC class II) haplotype which contains the peptide as described herein, in particular the peptide NQEESVRFDSDVGEFR (Hpep 1—SEQ ID NO:1) or a peptide with a length of 16 amino acids comprising the SDVGE-X-R (SEQ ID NO: 13) motif and having an amino acid sequence with at least 80, 85, 86, 87, 88, 90, 91, 92, 93, 94, 95, 96, 97, 98 or 99% identity with SEQ ID NO: 1. In one embodiment, the transplant or graft is from a human donor with a MHC class II haplotype which contains the peptide as described herein, in particular the peptide NQEESVRFDSDVGEFR (Hpep 1—SEQ ID NO:1) or a peptide with a length of 16 amino acids comprising the SDVGE-X-R (SEQ ID NO: 13) motif and having an amino acid sequence with at least 80, 85, 86, 87, 88, 90, 91, 92, 93, 94, 95, 96, 97, 98 or 99% identity with SEQ ID NO: 1.

In one embodiment, the transplant or graft, in particular stem cells such as hemopoietic stem cells, is inserted or is to be inserted into a human recipient with a major histocompatibility complex (MHC, e.g., MHC class I and/or MHC class II) haplotype which contains the peptide as described herein, in particular the peptide NQEESVRFDSDVGEFR (Hpep 1—SEQ ID NO:1) or a peptide with a length of 16 amino acids comprising the SDVGE-X-R (SEQ ID NO: 13) motif and having an amino acid sequence with at least 80, 85, 86, 87, 88, 90, 91, 92, 93, 94, 95, 96, 97, 98 or 99% identity with SEQ ID NO: 1. In one embodiment, the transplant or graft, in particular stem cells such as hemopoietic stem cells, is inserted or is to be inserted into a human recipient with a MHC class II haplotype which contains the peptide as described herein, in particular the peptide NQEESVRFDSDVGEFR (Hpep 1—SEQ ID NO:1) or a peptide with a length of 16 amino acids comprising the SDVGE-X-R (SEQ ID NO: 13) motif and having an amino acid sequence with at least 80, 85, 86, 87, 88, 90, 91, 92, 93, 94, 95, 96, 97, 98 or 99% identity with SEQ ID NO: 1.

As used herein, the term "transplant rejection" or "graft rejection" encompasses both acute and chronic transplant or graft rejection. "Acute rejection" is the rejection by the immune system of the recipient when the transplanted or grafted tissue is immunologically foreign. Acute rejection is characterized by infiltration of the transplant or graft tissue by immune cells of the recipient, which carry out their effector function and destroy the transplant or graft tissue. The onset of acute rejection is rapid and generally occurs in humans within a few weeks after transplant surgery. Generally, acute rejection can be inhibited or suppressed with immunosuppressive drugs such as rapamycin, cyclosporin and the like. "Chronic rejection" generally occurs in humans within several months to years after engraftment, even in the presence of successful immunosuppression of acute rejection. Fibrosis is a common factor in chronic rejection of all types of organ transplants.

Typically, the active ingredient of the present invention (i.e., the peptide, the immunoconjugate, and the nanoparticle herein disclosed) is administered or is to be administered to the subject at a therapeutically effective amount. By a "therapeutically effective amount" is meant a sufficient amount of the active ingredient of the present invention to induce tolerance or to reduce an immune response at a reasonable benefit/risk ratio applicable to any medical treatment. It will be understood that the total daily usage of the compounds and compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. In one embodiment, the peptide of the invention is used or to be used at a dose, preferably at a daily dose, of about 0.01, 0.05, 0.1, 0.5, 1.0, 2.5, 5.0, 10.0, 15.0, 25.0, 50.0, 100, 250 or 500 mg. In one embodiment, the peptide of the invention is used or to be used at a dose, preferably at a daily dose, of about 100, 120, 140, 160, 180, 200, 220, 240, 260, 280, 300, 320, 340, 360, 380, 400, 420, 440, 460, 480, 500, 520, 540, 560, 580 or 600 mg. A medicament typically contains from about 0.01 mg to about 500 mg of the active ingredient, in particular from 1 mg to about 100 mg of the active ingredient. In one embodiment, an effective amount of the peptide of the invention is administered or to be administered at a dosage level ranging from 0.0002 mg/kg to about 20 mg/kg of body weight per day, especially ranging from about 0.001 mg/kg to about 7 mg/kg of body weight per day. In one embodiment, an effective amount of the peptide of the invention is administered or to be administered at a dosage level ranging from 0.4 mg/kg/day (mg per g of body weight per day) to about 40 mg/kg/day, preferably of about 1 mg/kg/day to about 10 mg/kg/day.

In one embodiment, the active ingredient of the present invention (i.e., the peptide, the immunoconjugate, and the nanoparticle herein disclosed) is administered or is to be administered to the patient in need thereof prior to a transplant or graft. In one embodiment, the active ingredient of the present invention (i.e., the peptide, the immunoconjugate, and the nanoparticle herein disclosed) is administered or is to be administered to the patient in need thereof at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 day(s) prior to a transplant or graft. In one embodiment, the active ingredient of the present invention (i.e., the peptide, the immunoconjugate, and the nanoparticle herein disclosed) is administered or is to be administered to the patient in need thereof at least 1, 2 or 3 month(s) prior to a transplant or graft. In one embodiment, the active ingredient of the present invention (i.e., the peptide, the immunoconjugate, and the nanoparticle herein disclosed) is administered or is to be administered to the patient in need thereof after a transplant or graft. In one embodiment, the active ingredient of the present invention (i.e., the peptide, the immunoconjugate, and the nanoparticle herein disclosed) is administered or is to be administered to the patient in need thereof concomitantly with a transplant or graft. In one embodiment, the active ingredient of the present invention (i.e., the peptide, the immunoconjugate, and the nanoparticle herein disclosed) is administered or is to be administered to the patient in need thereof concomitantly with a transplant or graft and continuously thereafter.

In one embodiment, the active ingredient of the present invention (i.e., the peptide, the immunoconjugate, and the nanoparticle herein disclosed) is administered or is to be administered to the patient in need thereof with at least one immunosuppressive agent.

Examples of immunosuppressive agents include, without being limited to, corticosteroids such as budesonide, prednisone, prednisolone, methylprednisolone; cyclosporine; tacrolimus; sirolimus; azathioprine.

In one embodiment, the at least one immunosuppressive agent is a corticosteroid.

In some embodiments, the peptide of the present invention is loaded in MHC class I multimers. Typically, MHC class I multimers are well known in the art and include but are not limited to dimers, tetramers, pentamers, streptamers, dextramers and octamers.

Accordingly, the present invention also relates to a MHC/peptide multimer, also known as a MHC/peptide complex, wherein said MHC/peptide multimer is a MHC class I multimer loaded with the peptide as described hereinabove.

In one embodiment, the MHC/peptide multimer of the present invention is a MHC class I multimer loaded with the peptide NQEESVRFDSDVGEFR (Hpep 1—SEQ ID NO:1) or a peptide with a length of 16 amino acids comprising the SDVGE-X-R (SEQ ID NO: 13) motif and having an amino acid sequence with at least 80, 85, 86, 87, 88, 90, 91, 92, 93, 94, 95, 96, 97, 98 or 99% identity with SEQ ID NO: 1. In one embodiment, the MHC/peptide multimer of the present invention is a MHC class I multimer loaded with the peptide NQEESVRFDSDVGEFR (Hpep 1—SEQ ID NO:1) or a peptide having an amino acid sequence as set forth in SEQ ID NO: 1 with a substitution of one or two amino acid(s) of SEQ ID NO: 1, provided that said substitution is not within the SDVGE-X-R (SEQ ID NO: 13) motif.

As used herein, the term "Major Histocompatibility Complex" (MHC) is a generic designation meant to encompass the histo-compatibility antigen systems described in different species including the human leucocyte antigens (HLA). As used herein, the term "MHC/peptide multimer" refers to a stable multimeric complex composed of major histocompatibility complex (MHC) protein subunits loaded with a peptide of the invention. According to the invention, said MHC/peptide multimer (also called herein MHC/peptide complex) include, but are not limited to, a MHC/peptide dimer, trimer, tetramer or pentamer. In humans there are three major different genetic loci that encode MHC class I molecules (the MHC-molecules of the human are also designated human leukocyte antigens (HLA)): HLA-A, HLA-B, and HLA-C. HLA-A*01, HLA-A*02, and HLA-A*11 are examples of different MHC class I alleles that can be expressed from these loci. It should be further noted that nonclassical human MHC class I molecules such as HLA-E (functional homolog in mice is called Qa-1b) and MICA/B molecules are also encompassed within the context of the invention. In some embodiments, the MHC/peptide multimer is a HLA/peptide multimer selected from the group consisting of HLA-A/peptide multimer, HLA-B/peptide multimer, HLA-C/peptide multimer, HLA-E/peptide multimer, MICA/peptide multimer and MICB/peptide multimer. Methods for obtaining MHC/peptide tetramers are described in WO96/26962 and WO01/18053, which are incorporated by reference. The MHC/peptide multimer may be a multimer where the heavy chain of the MHC is biotinylated, which allows combination as a tetramer with streptavidin. Such MHC-peptide tetramer has an increased avidity for the appropriate TCR-carrier T lymphocytes and can therefore be used to visualize reactive populations by immunofluorescence. The multimers can also be attached to paramagnetic particles or magnetic beads to facilitate removal of non-specifically bound reporter and cell sorting. Such particles are readily available from commercial sources (e.g., Beckman Coulter, Inc., San Diego, Calif, USA). Multimer staining does not kill the labeled cells; therefore, cell integrity is maintained for further analysis. In some embodiments, the MHC/peptide multimer of the present invention is particularly suitable for isolating or identifying a population of $CD8^+CD45RC^{low}$ Tregs (in a flow cytometry assay).

Accordingly, a further object of the present invention relates to a method for isolating and expanding a population of $CD8^+CD45RC^{low}$ Tregs specifically recognizing the peptide of the invention, comprising a step of isolating a population of $CD8^+CD45RC^{low}$ Tregs by MHC/peptide multimer staining with the MHC class I multimer of the invention, and then a step of expanding the isolated population of $CD8^+CD45RC^{low}$ Tregs with polyclonal stimulation.

In one embodiment, MHC/peptide multimer staining encompasses the staining $CD8^+CD45RC^{low}$ Tregs with the MHC class I multimer of the invention and the subsequent sorting of the stained $CD8^+CD45RC^{low}$ Tregs, preferably the sorting is a FACS sorting such as, for example, a FACS Aria sorting.

Examples or polyclonal stimulation (also referred to as polyclonal activation) includes, without being limited to, stimulation with anti-CD3 antibodies (Abs) and anti-CD28 antibodies (Abs), in particular stimulation with anti-CD3 monoclonal antibodies (mAbs) and anti-CD28 monoclonal antibodies (mAbs); stimulation with anti-CD3 antibodies (Abs), in particular stimulation with anti-CD3 monoclonal antibodies (mAbs); stimulation with phytohemagglutinin.

In one embodiment, the polyclonal stimulation is a stimulation with anti-CD3 Abs and anti-CD28 Abs, in particular a stimulation with anti-CD3 mAbs and anti-CD28 mAbs.

In one embodiment, the population of $CD8^+CD45RC^{low}$ Tregs is isolated from a donor subject (i.e., a subject from whom a transplant or graft is originating) or from a recipient patient (i.e., a patient who received, is receiving or is awaiting the receipt of a transplant or a graft).

In one embodiment, the population of $CD8^+CD45RC^{low}$ Tregs is isolated from a donor subject, in particular from a subject from whom a solid organ transplant is originating. In one embodiment, the population of $CD8^+CD45RC^{low}$ Tregs is isolated from a recipient patient, in particular from a patient who received, is receiving or is awaiting the receipt of stem cells, such as hematopoietic stem cells.

The peptide and multimer herein disclosed are also suitable for expanding and stimulating a population of $CD8^+CD45RC^{low}$ Tregs in its immunosuppressive activity. In other words, the peptide and multimer herein disclosed are also suitable for expanding a population of $CD8^+CD45RC^{low}$ Tregs and stimulating the immunosuppressive activity of said population of $CD8^+CD45RC^{low}$ Tregs.

Accordingly, a further object of the present invention relates to a method for expanding and stimulating a population of $CD8^+CD45RC^{low}$ Tregs in its immunosuppressive activity, comprising a step of culturing a population of $CD8^+CD45RC^{low}$ Tregs with a culture medium comprising the peptide of the present invention in presence of a population of antigen presenting cells (APCs), such as a population of dendritic cells.

A further object of the present invention is thus a method for expanding a population of $CD8^+CD45RC^{low}$ Tregs and for stimulating its immunosuppressive activity, comprising a step of culturing a population of $CD8^+CD45RC^{low}$ Tregs with a culture medium comprising the peptide of the present invention in presence of a population of antigen presenting cells (APCs), such as a population of dendritic cells.

The terms "low" or "low/−", as used herein in relation to $CD45RC^{low}$ Tregs or $CD45RC^{low/-}$ Tregs, are well known in the art and refer to the expression level by the Tregs of the cell marker of interest, i.e., CD45RC, in that said expression level is low by comparison with the expression level of that cell marker in a population of Tregs being analyzed as a whole. More particularly, the terms "low" or "low/−" refer to a distinct population of Tregs that expresses the cell marker, i.e., CD45RC, at a level lower than one or more other distinct population of Tregs.

Thus, as used in the present invention, the population of $CD8^+CD45RC^{low}$ Tregs may be referred to as a population of $CD8^+CD45RC^{low/-}$ Tregs. Accordingly, in one embodiment, the population of $CD8^+CD45RC^{low}$ Tregs is a population of $CD8^+CD45RC^{low/-}$ Tregs.

As used herein, the term "expanding" refers to the process of converting and/or amplifying a given population of cells (e.g., Tregs such as $CD8^+CD45RC^{low}$ Tregs).

In a particular embodiment, the method of the invention for expanding a population of $CD8^+CD45RC^{low}$ Tregs and for stimulating its immunosuppressive activity is an in vitro method.

In one embodiment, the method of the invention for expanding and stimulating a population of $CD8^+CD45RC^{low}$ Tregs in its immunosuppressive activity comprises a step of culturing a population of $CD8^+CD45RC^{low}$ Tregs with a culture medium comprising the peptide NQEESVRFDSDVGEFR (Hpep 1—SEQ ID NO:1) or a peptide with a length of 16 amino acids comprising the SDVGE-X-R (SEQ ID NO: 13) motif and having an amino acid sequence with at least 80, 85, 86, 87, 88, 90, 91, 92, 93, 94, 95, 96, 97, 98 or 99% identity with SEQ ID NO: 1 in presence of a population of antigen presenting cells (APCs), such as a population of dendritic cells.

In one embodiment, the method of the invention for expanding and stimulating a population of $CD8^+$ $CD45RC^{low}$ Tregs in its immunosuppressive activity comprises a step of culturing a population of $CD8^{+}CD45RC^{low}$ Tregs with a culture medium comprising the peptide NQEESVRFDSDVGEFR (Hpep 1—SEQ ID NO:1) or a peptide having an amino acid sequence as set forth in SEQ ID NO: 1 with a substitution of one or two amino acid(s) of SEQ ID NO: 1, provided that said substitution is not within the SDVGE-X-R (SEQ ID NO: 13) motif, in presence of a population of antigen presenting cells (APCs), such as a population of dendritic cells.

In one embodiment, the population of antigen presenting cells (APCs) is a population of dendritic cells, monocytes and/or artificial antigen presenting cells (aAPCs).

A used herein, "artificial antigen presenting cells (aAPCs)" refers to cell lines expressing a MHC-I that can be loaded with a peptide of interest, such as the human MHC-derived human peptide of the invention. For example, artificial antigen presenting cells (aAPCs) are described in Butler et al., Clin Cancer Res. 2007 Mar. 15; 13(6):1857-67. Examples of aAPCs thus include the $aAPC^{33}$ cell line described in Butler et al., Clin Cancer Res. 2007 Mar. 15; 13(6):1857-67.

In one embodiment, the population of antigen presenting cells (APCs) is a population of dendritic cells.

In one embodiment, the population of dendritic cells is a population of plasmacytoid dendritic cells (pDCs). In some embodiments, the pDCs are mature pDCs.

As used herein, the term "culture medium" refers to any medium capable of supporting the growth and the differentiation of T cells into regulatory T cells. Typically, it consists of a base medium containing nutrients (a source of carbon, amino acids), a pH buffer and salts, which can be supplemented with growth factors and/or antibiotics. In one embodiment, the base medium can be RPMI 1640, DMEM, IMDM, X-VIVO or AIM-V medium, all of which are commercially available standard media. In one embodiment, the base medium can be Texmacs, RPMI 1640, DMEM, IMDM, X-VIVO or AIM-V LymphoOne, CTS Optimizer, Immunocult, or Prime XV medium, all of which are commercially available standard GMP (good manufacturing practice) media. Preferred media formulations that will support the growth and the differentiation of naive T cells into regulatory T cells include chemically defined medium (CDM). As used herein, the term "chemically defined medium" (CDM) refers to a nutritive solution for culturing cells which contains only specified components, preferably components of known chemical structure. A chemically defined medium is a serum-free and/or a feeder-free medium. In one embodiment, the culture medium may be supplemented with purified human albumin (Vialebex) or CTS Optimizer serum replacement.

The step of culturing the population of $CD8^{+}CD45RC^{low}$ Tregs with the peptide of the invention in the presence of a population of pDCs shall be carried out for the necessary time required for the presentation of said peptide by the pDCs to the $CD8^{+}CD45RC^{low}$ Tregs. Typically, the culture of a population of $CD8^{+}$ Tregs with the peptide of the invention in the presence of a population of pDCs shall be carried from 1 day to 1 week or more.

In some embodiments, the method may comprise an additional step of isolating the population of $CD8^{+}$ $CD45RC^{low}$ Tregs thus generated.

Alternatively, the invention relates to a method for expanding and stimulating a population of $CD8^{+}$ $CD45RC^{low}$ Tregs in its immunosuppressive activity, comprising a step of culturing a population of $CD8^{+}CD45RC^{low}$ Tregs with a culture medium comprising the MHC/peptide multimer of the present invention.

In some embodiments, the multimer is coated on a nanoparticle.

The method for expanding and stimulating the population of $CD8^{+}CD45RC^{low}$ Tregs in its immunosuppressive activity are particularly useful for adoptive T cell transfer for preventing transplant or graft rejection or GVHD.

Another object of the invention is a population of $CD8^{+}$ $CD45RC^{low}$ Tregs susceptible to be obtained, or obtainable, by the method for expanding and stimulating the population of $CD8^{+}CD45RC^{low}$ Tregs in its immunosuppressive activity as described hereinabove.

Another object of the invention is said population of $CD8^{+}CD45RC^{low}$ Tregs susceptible to be obtained, or obtainable, by the method of the invention, for use as a medicament.

Another object of the invention is said population of $CD8^{+}CD45RC^{low}$ Tregs susceptible to be obtained, or obtainable, by the method of the invention, for use in inducing immune tolerance and/or for use in reducing an immune response.

A further object of the invention is said population of $CD8^{+}CD45RC^{low}$ Tregs susceptible to be obtained, or obtainable, by the method of the invention, for use in preventing or reducing transplant or graft rejection or graft versus host disease (GVHD).

A further object of the present invention relates to an antibody that specifically binds to a peptide or a multimer of the present invention.

In one embodiment, the antibody of the invention specifically binds the peptide NQEESVRFDSDVGEFR (Hpep 1—SEQ ID NO:1) or a peptide with a length of 16 amino acids comprising the SDVGE-X-R (SEQ ID NO: 13) motif and having an amino acid sequence with at least 80, 85, 86, 87, 88, 90, 91, 92, 93, 94, 95, 96, 97, 98 or 99% identity with SEQ ID NO: 1 or specifically binds a MHC class I multimer loaded with one of said peptides.

In one embodiment, the antibody of the invention specifically binds the peptide NQEESVRFDSDVGEFR (Hpep 1—SEQ ID NO:1) or a peptide having an amino acid sequence as set forth in SEQ ID NO: 1 with a substitution of one or two amino acid(s) of SEQ ID NO: 1, provided that said substitution is not within the SDVGE-X-R (SEQ ID NO: 13) motif, or specifically binds a MHC class I multimer loaded with one of said peptides.

As used herein, the term "antibody" has its general meaning in the art and encompasses monoclonal antibodies (including full-length monoclonal antibodies), polyclonal antibodies, multispecific antibodies (e.g., bispecific antibodies) formed from at least two intact antibodies, human antibodies, humanized antibodies, camelised antibodies, chimeric antibodies, single-chain Fvs (scFv), single-chain antibodies, single domain antibodies, domain antibodies, Fab fragments, $F(ab')_2$ fragments, antibody fragments that exhibit the desired biological activity, disulfide-linked Fvs (sdFv), and anti-idiotypic (anti-Id) antibodies (including, e.g., anti-Id antibodies to antibodies of the invention), intrabodies, and epitope-binding fragments of any of the above. In particular, antibodies include immunoglobulin molecules and immunologically active fragments of immunoglobulin molecules, i.e., molecules that contain an antigen-binding site. Immunoglobulin molecules can be of any type (e.g., IgG, IgE, IgM, IgD, IgA and IgY), class (e.g., IgG1, IgG2, IgG3, IgG4, IgA1 and IgA2) or subclass.

As used herein the term "bind" indicates that the antibody has affinity for the peptide. The term "affinity", as used herein, means the strength of the binding of an antibody to an epitope. The affinity of an antibody is given by the dissociation constant Kd, defined as [Ab]33 [Ag]/[Ab–Ag], where [Ab–Ag] is the molar concentration of the antibody-antigen complex, [Ab] is the molar concentration of the unbound antibody and [Ag] is the molar concentration of the unbound antigen. The affinity constant Ka is defined by 1/Kd. Preferred methods for determining the affinity of mAbs can be found in Harlow, et al., Antibodies: A Laboratory Manual, Cold Spring Harbor Laboratory Press, Cold Spring Harbor, N.Y., 1988), Coligan et al., eds., Current Protocols in Immunology, Greene Publishing Assoc. and Wiley Interscience, N.Y., (1992, 1993), and Muller, Meth. Enzymol. 92:589-601 (1983), which references are entirely incorporated herein by reference. One preferred and standard method well known in the art for determining the affinity of mAbs is the use of Biacore instruments.

In some embodiments, the antibody of the present invention is a monoclonal antibody. The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, monoclonal antibodies are advantageous in that they can be synthesized by hybridoma cells that are uncontaminated by other immunoglobulin producing cells. Alternative production methods are known to those trained in the art, for example, a monoclonal antibody may be produced by cells stably or transiently transfected with the heavy and light chain genes encoding the monoclonal antibody.

Monoclonal antibodies may be generated using the method of Kohler and Milstein (Nature, 256:495, 1975). To prepare monoclonal antibodies useful in the invention, a mouse or other appropriate host animal is immunized at suitable intervals (e.g., twice-weekly, weekly, twice-monthly or monthly) with the appropriate antigenic forms (e.g., the peptide or the multimer of the present invention). The animal may be administered a final "boost" of antigen within one week of sacrifice. It is often desirable to use an immunologic adjuvant during immunization. Suitable immunologic adjuvants include Freund's complete adjuvant, Freund's incomplete adjuvant, alum, Ribi adjuvant, Hunter's Titermax, saponin adjuvants such as QS21 or Quil A, or CpG-containing immunostimulatory oligonucleotides. Other suitable adjuvants are well-known in the field. The animals may be immunized by subcutaneous, intraperitoneal, intramuscular, intravenous, intranasal or other routes. A given animal may be immunized with multiple forms of the antigen by multiple routes. Following the immunization regimen, lymphocytes are isolated from the spleen, lymph node or other organ of the animal and fused with a suitable myeloma cell line using an agent such as polyethylene glycol to form a hybridoma. Following fusion, cells are placed in media permissive for growth of hybridomas but not the fusion partners using standard methods. Following culture of the hybridomas, cell supernatants are analysed for the presence of antibodies of the desired specificity, i.e., that selectively bind the antigen. Suitable analytical techniques include ELISA, flow cytometry, immunoprecipitation, and western blotting. Other screening techniques are well-known in the field. Preferred techniques are those that confirm binding of antibodies to conformationally intact, natively folded antigen, such as non-denaturing ELISA, flow cytometry, and immunoprecipitation.

In some embodiments, the monoclonal antibody of the invention is a chimeric antibody, in particular a chimeric mouse/human antibody. As used herein, the term "chimeric antibody" refers to an antibody which comprises a VH domain and a VL domain of a non-human antibody, and a CH domain and a CL domain of a human antibody. In some embodiments, the human chimeric antibody of the present invention can be produced by obtaining nucleic sequences encoding VL and VH domains as previously described, constructing a human chimeric antibody expression vector by inserting them into an expression vector for animal cell having genes encoding human antibody CH and human antibody CL, and expressing the coding sequence by introducing the expression vector into an animal cell. As the CH domain of a human chimeric antibody, it may be any region which belongs to human immunoglobulin, but those of IgG class are suitable and any one of subclasses belonging to IgG class, such as IgG1, IgG2, IgG3 and IgG4, can also be used. Also, as the CL of a human chimeric antibody, it may be any region which belongs to Ig, and those of kappa class or lambda class can be used. Methods for producing chimeric antibodies involve conventional recombinant DNA and gene transfection techniques are well known in the art (See Morrison SL. et al. (1984) and patent documents U.S. Pat. Nos. 5,202,238; and 5,204,244).

In some embodiments, the monoclonal antibody of the invention is a humanized antibody. In particular, in said humanized antibody, the variable domain comprises human acceptor frameworks regions, and optionally human constant domain where present, and non-human donor CDRs, such as mouse CDRs. According to the invention, the term "humanized antibody" refers to an antibody having variable region framework and constant regions from a human antibody but retains the CDRs of a previous non-human antibody. The humanized antibody of the present invention may be produced by obtaining nucleic acid sequences encoding CDR domains, as previously described, constructing a humanized antibody expression vector by inserting them into an expression vector for animal cell having genes encoding (i) a heavy chain constant region identical to that of a human antibody and (ii) a light chain constant region identical to that of a human antibody, and expressing the genes by introducing the expression vector into an animal cell. The humanized antibody expression vector may be either of a type in which a gene encoding an antibody heavy chain and a gene encoding an antibody light chain exists on separate vectors or of a type in which both genes exist on the same vector (tandem type). In respect of easiness of construction of a humanized antibody expression vector, easiness of introduction into animal cells, and balance between the expression levels of antibody H and L chains in animal cells, humanized antibody expression vector of the tandem type is preferred. Examples of tandem type humanized antibody expression vector include pKANTEX93 (WO 97/10354), pEE18 and the like. Methods for producing humanized antibodies based on conventional recombinant DNA and gene transfection techniques are well known in the art (See, e. g., Riechmann L. et al. 1988; Neuberger MS. et al. 1985). Antibodies can be humanized using a variety of techniques known in the art including, for example, CDR-grafting (EP 239,400; PCT publication WO91/09967; U.S. Pat. Nos. 5,225,539; 5,530,101; and 5,585,089), veneering or resurfacing (EP 592,106; EP 519,596; Padlan EA (1991);

Studnicka G M et al. (1994); Roguska MA. et al. (1994)), and chain shuffling (U.S. Pat. No. 5,565,332). The general recombinant DNA technology for preparation of such antibodies is also known (see European Patent Application EP 125023 and International Patent Application WO 96/02576).

In some embodiments the antibody of the invention is a human antibody. As used herein the term "human antibody" is intended to include antibodies having variable and constant regions derived from human immunoglobulin sequences. The human antibodies of the present invention may include amino acid residues not encoded by human immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences. Human antibodies can be produced using various techniques known in the art. Human antibodies are described generally in van Dijk and van de Winkel, Cur. Opin. Pharmacol. 5; 368-74 (2001) and Lonberg, Cur. Opin. Immunol. 20; 450-459 (2008). Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23; 1117-1125 (2005). See also, e.g., U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application publication No. US 2007/0061900, describing VELOCIMOUSE® technology. Human variable regions from intact antibodies generated by such animals may be further modified, e.g., by combining with a different human constant region. Human antibodies can also be made by hybridoma-based methods. Human myeloma and mouse-human heteromyeloma cell lines for the production of human monoclonal antibodies have been described. (See, e.g., Kozbor J. Immunol., 13: 3001 (1984); Brodeur et al., Monoclonal Antibody Production Techniques and Applications, pp. 51-63 (Marcel Dekker, Inc., New York, 1987); and Boerner et al., J. Immunol., 147: 86(1991). Human antibodies generated via human B-cell hybridoma technology are also described in Li et al., Proc. Natl. Acad. Sci. USA, 103:3557-3562 (2006). Additional methods include those described, for example, in U.S. Pat. No. 7,189,826 (describing production of monoclonal human igM antibodies from hybridoma cell lines) and Ni, Xiandai Mianyixue, 26(4): 265-268 (2006) (describing human-human hybridomas). Human hybridoma technology (Trioma technology) is also described in Vollmers and Brandlein, Histology and Histopathology, 20(3):927-937 (2005) and Vollmers and Brandlein, Methods and Findings in Experimental and Clinical Pharmacology, 27(3):185-91 (2005). Fully human antibodies can also be derived from phage-display libraries (as disclosed in Hoogenboom et al., 1991, J. Mol. Biol. 227: 381; and Marks et al., 1991, J. Mol. Biol. 222:581). Phage display techniques mimic immune selection through the display of antibody repertoires on the surface of filamentous bacteriophage, and subsequent selection of phage by their binding to an antigen of choice. One such technique is described in PCT publication No. WO 99/10494. Human antibodies described herein can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

The antibody herein disclosed is particularly suitable for preventing transplant or graft rejection or GVHD. In particular, the antibody that specifically binds to the multimer of the present invention would be suitable for depleting dendritic cells that present the peptide of the present invention.

As used herein, the term "deplete" with respect to dendritic cells, refers to a measurable decrease in the number of dendritic cells in the subject. The reduction can be at least about 10%, e.g., at least about 20%, 30%, 40%, 50%, 60%, 70%, 80%, 90%, 95%, 96%, 97%, 98%, 99%, or more. In some embodiments, the term refers to a decrease in the number of dendritic cells in a subject or in a sample to an amount below detectable limits.

In some embodiments, the antibody of the present invention mediates antibody-dependent cell-mediated cytotoxicity. As used herein the term "antibody-dependent cell-mediated cytotoxicity" or 'ADCC" refer to a cell-mediated reaction in which non-specific cytotoxic cells (e.g., Natural Killer (NK) cells, neutrophils, and macrophages) recognize bound antibody on a target cell and subsequently cause lysis of the target cell. While not wishing to be limited to any particular mechanism of action, these cytotoxic cells that mediate ADCC generally express Fc receptors (FcRs).

As used herein "Fc region" includes the polypeptides comprising the constant region of an antibody excluding the first constant region immunoglobulin domain. Thus, Fc refers to the last two constant region immunoglobulin domains of IgA, IgD, and IgG, and the last three constant region immunoglobulin domains of IgE and IgM, and the flexible hinge N-terminal to these domains. For IgA and IgM Fc may include the J chain. For IgG, Fc comprises immunoglobulin domains Cgamma2 and Cgamma3 (Cγ2 and Cγ3) and the hinge between Cgamma1 (Cγ1) and Cgamma2 (Cγ2). Although the boundaries of the Fc region may vary, the human IgG heavy chain Fc region is usually defined to comprise residues C226 or P230 to its carboxyl-terminus, wherein the numbering is according to the EU index as in Kabat et al. (1991, NIH Publication 91-3242, National Technical Information Service, Springfield, Va.). The "EU index as set forth in Kabat" refers to the residue numbering of the human IgG1 EU antibody as described in Kabat et al. supra. Fc may refer to this region in isolation, or this region in the context of an antibody, antibody fragment, or Fc fusion protein. An Fc variant protein may be an antibody, Fc fusion, or any protein or protein domain that comprises an Fc region. Particularly preferred are proteins comprising variant Fc regions, which are non-naturally occurring variants of an Fc region. The amino acid sequence of a non-naturally occurring Fc region (also referred to herein as a "variant Fc region") comprises a substitution, insertion and/or deletion of at least one amino acid residue compared to the wild type amino acid sequence. Any new amino acid residue appearing in the sequence of a variant Fc region as a result of an insertion or substitution may be referred to as a non-naturally occurring amino acid residue. Note: Polymorphisms have been observed at a number of Fc positions, including but not limited to Kabat 270, 272, 312, 315, 356, and 358, and thus slight differences between the presented sequence and sequences in the prior art may exist.

The terms "Fc receptor" or "FcR" are used to describe a receptor that binds to the Fc region of an antibody. The primary cells for mediating ADCC, NK cells, express FcγRIII, whereas monocytes express FcγRI, FcγRII, FcγRIII and/or FcγRIV. FcR expression on hematopoietic cells is summarized in Ravetch and Kinet, Annu. Rev. Immunol., 9:457-92 (1991). To assess ADCC activity of a molecule, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecules of interest may be assessed in vivo, e.g., in an animal model such as that disclosed in Clynes et al., Proc. Natl. Acad. Sci. (USA), 95:652-656 (1998). As used herein, the term "Effector cells" refers to leukocytes which express one or more FcRs and perform effector functions. The cells express at least FcγRI, FCγRII, FcγRIII and/or FcγRIV and carry out ADCC effector function. Examples of human leukocytes which mediate ADCC include peripheral blood mononuclear cells (PBMC), natural killer (NK) cells, monocytes, cytotoxic T cells and neutrophils.

In some embodiments, the antibody of the present invention is a full-length antibody. In some embodiments, the full-length antibody is an IgG1 antibody. In some embodiments, the full-length antibody is an IgG3 antibody.

In some embodiments, the antibody of the present invention comprises a variant Fe region that has an increased affinity for FcγRIA, FcγRIIA, FcγRIIB, FcγRIIIA, FcγRIIIB, and FcγRIV. In some embodiments, the antibody of the present invention comprises a variant Fe region comprising at least one amino acid substitution, insertion or deletion wherein said at least one amino acid residue substitution, insertion or deletion results in an increased affinity for FcγRIA, FcγRIIA, FcγRIIB, FcγRIIIA, FcγRIIIB, and FcγRIV, In some embodiments, the antibody of the present invention comprises a variant Fc region comprising at least one amino acid substitution, insertion or deletion wherein said at least one amino acid residue is selected from the group consisting of: residue 239, 330, and 332, wherein amino acid residues are numbered following the EU index. In some embodiments, the antibody of the present invention comprises a variant Fc region comprising at least one amino acid substitution wherein said at least one amino acid substitution is selected from the group consisting of: S239D, A330L, A330Y, and 1332E, wherein amino acid residues are numbered following the EU index.

In some embodiments, the glycosylation of the antibody is modified. For example, an aglycoslated antibody can be made (i.e., the antibody lacks glycosylation). Glycosylation can be altered to, for example, increase the affinity of the antibody for the antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al. Additionally or alternatively, an antibody can be made that has an altered type of glycosylation, such as a hypofucosylated or non-fucosylated antibody having reduced amounts of or no fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the present invention to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation or are devoid of fucosyl residues. Therefore, in some embodiments, the human monoclonal antibodies of the present invention may be produced by recombinant expression in a cell line which exhibit hypofucosylation or non-fucosylation pattern, for example, a mammalian cell line with deficient expression of the FUT8 gene encoding fucosyltransferase. PCT Publication WO 03/035835 by Presta describes a variant CHO cell line, Lecl3 cells, with reduced ability to attach fucose to Asn(297)-linked carbohydrates, also resulting in hypofucosylation of antibodies expressed in that host cell (see also Shields, R. L. et al, 2002 J. Biol. Chem. 277:26733-26740). PCT Publication WO 99/54342 by Umana et al. describes cell lines engineered to express glycoprotein-modifying glycosyl transferases (e.g., beta(1, 4)-N acetylglucosaminyltransferase III (GnTIII)) such that antibodies expressed in the engineered cell lines exhibit increased bisecting GlcNac structures which results in increased ADCC activity of the antibodies (see also Umana et al, 1999 Nat. Biotech. 17: 176-180). Eureka Therapeutics further describes genetically engineered CHO mammalian cells capable of producing antibodies with altered mammalian glycosylation pattern devoid of fucosyl residues (http://www.eurekainc.com/a&boutus/companyoverview.html). Alternatively, the human monoclonal antibodies of the present invention can be produced in yeasts or filamentous fungi engineered for mammalian-like glycosylation pattern and capable of producing antibodies lacking fucose as glycosylation pattern (see for example EP1297172B1).

In some embodiments, the antibody of the present invention mediates complement dependent cytotoxicity. "Complement dependent cytotoxicity" or "CDC" refers to the ability of a molecule to initiate complement activation and lyse a target in the presence of complement. The complement activation pathway is initiated by the binding of the first component of the complement system (C1q) to a molecule (e.g., an antibody) complexed with a cognate antigen. To assess complement activation, a CDC assay, e.g., as described in Gazzano-Santaro et al., J. Immunol. Methods, 202:163 (1996), may be performed.

In some embodiments, the antibody of the present invention mediates antibody-dependent phagocytosis. As used herein, the term "antibody-dependent phagocytosis" or "opsonisation" refers to the cell-mediated reaction wherein nonspecific cytotoxic cells that express FcγRs recognize bound antibody on a target cell and subsequently cause phagocytosis of the target cell.

In some embodiments, the antibody of the present invention is conjugated to a therapeutic moiety, i.e., a drug. The therapeutic moiety can be, e.g., a cytotoxin, a chemotherapeutic agent, a cytokine, an immunosuppressant, an immune stimulator, a lytic peptide, or a radioisotope. Such conjugates are referred to herein as an "antibody-drug conjugates" or "ADCs".

In some embodiments, the antibody of the present invention is conjugated to a cytotoxic moiety. The cytotoxic moiety may, for example, be selected from the group consisting of taxol; cytochalasin B; gramicidin D; ethidium bromide; emetine; mitomycin; etoposide; tenoposide; vincristine; vinblastine; colchicine; doxorubicin; daunorubicin; dihydroxy anthracin dione; a tubulin-inhibitor such as maytansine or an analog or derivative thereof; an antimitotic agent such as monomethyl auristatin E or F or an analog or derivative thereof; dolastatin 10 or 15 or an analogue thereof; irinotecan or an analogue thereof; mitoxantrone; mithramycin; actinomycin D; 1-dehydrotestosterone; a glucocorticoid; procaine; tetracaine; lidocaine; propranolol; puromycin; calicheamicin or an analog or derivative thereof; an antimetabolite such as methotrexate, 6 mercaptopurine, 6 thioguanine, cytarabine, fludarabine, 5 fluorouracil, dacarbazine, hydroxyurea, asparaginase, gemcitabine, or cladribine; an alkylating agent such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C; a platinum derivative such as cisplatin or carboplatin; duocarmycin A, duocarmycin SA, rachelmycin (CC-1065), or an analog or derivative thereof; an antibiotic such as dactinomycin, bleomycin, daunorubicin, doxorubicin, idarubicin, mithramycin, mitomycin, mitoxantrone, plicamycin, anthramycin (AMC)); pyrrolo[2,1-c][1,4]-benzodiazepines (PDB); diphtheria toxin and related molecules such as diphtheria A chain and active fragments thereof and hybrid molecules, ricin toxin such as ricin A or a deglycosylated ricin A chain toxin, cholera toxin, a Shiga-like toxin such as SLT I, SLT II, SLT IIV, LT toxin, C3 toxin, Shiga toxin, pertussis toxin, tetanus toxin, soybean Bowman-Birk protease inhibitor, *Pseudomonas* exotoxin, alorin, saporin, modeccin, gelanin, abrin A chain, modeccin A chain, alpha-sarcin, *Aleurites fordii* proteins, dianthin proteins, *Phytolacca americana* proteins such as PAPI, PAPII, and PAP-S, *Momordica charantia* inhibitor, curcin, crotin, *Sapaonaria officinalis* inhibitor, gelonin, mitogellin, restrictocin, phenomycin, and enomycin toxins; ribonuclease (RNase); DNase I; Staphylococcal enterotoxin A; pokeweed antiviral protein; diphtherin toxin; and *Pseudomonas* endotoxin.

In some embodiments, the antibody of the present invention is conjugated to an auristatin or a peptide analog, derivative or prodrug thereof. Auristatins have been shown to interfere with microtubule dynamics, GTP hydrolysis and nuclear and cellular division (Woyke et al (2001) Antimicrob. Agents and Chemother. 45(12): 3580-3584) and have anti-cancer (U.S. Pat. No. 5,663,149) and antifungal activity (Pettit et al., (1998) Antimicrob. Agents and Chemother. 42: 2961-2965. For example, auristatin E can be reacted with para-acetyl benzoic acid or benzoylvaleric acid to produce AEB and AEVB, respectively. Other typical auristatin derivatives include AFP, MMAF (monomethyl auristatin F), and MMAE (monomethyl auristatin E). Suitable auristatins and auristatin analogs, derivatives and prodrugs, as well as suitable linkers for conjugation of auristatins to Abs, are described in, e.g., U.S. Pat. Nos. 5,635,483, 5,780,588 and 6,214,345 and in International patent application publications WO02088172, WO2004010957, WO2005081711, WO2005084390, WO2006132670, WO03026577, WO200700860, WO207011968 and WO205082023.

In some embodiments, the antibody of the present invention is conjugated to pyrrolo[2,1-c][1,4]-benzodiazepine (PDB) or an analog, derivative or prodrug thereof. Suitable PDBs and PDB derivatives, and related technologies are described in, e.g., Hartley J. A. et al., Cancer Res 2010; 70(17): 6849-6858; Antonow D. et al., Cancer J 2008; 14(3): 154-169; Howard P. W. et al., Bioorg Med Chem Lett 2009; 19: 6463-6466 and Sagnou et al., Bioorg Med Chem Lett 2000; 10(18): 2083-2086.

In some embodiments, the antibody of the present invention is conjugated to a cytotoxic moiety selected from the group consisting of an anthracycline, maytansine, calicheamicin, duocarmycin, rachelmycin (CC-1065), dolastatin 10, dolastatin 15, irinotecan, monomethyl auristatin E, monomethyl auristatin F, a PDB, and an analog, derivative, or prodrug of any thereof.

In some embodiments, the antibody of the present invention is conjugated to an anthracycline or an analog, derivative or prodrug thereof. In some embodiments, the antibody is conjugated to maytansine or an analog, derivative or prodrug thereof. In some embodiments, the antibody is conjugated to calicheamicin or an analog, derivative or prodrug thereof. In some embodiments, the antibody is conjugated to duocarmycin or an analog, derivative or prodrug thereof. In some embodiments, the antibody is conjugated to rachelmycin (CC-1065) or an analog, derivative or prodrug thereof. In some embodiments, the antibody is conjugated to dolastatin 10 or an analog, derivative or prodrug thereof. In some embodiments, the antibody is conjugated to dolastatin 15 or an analog, derivative or prodrug thereof. In some embodiments, the antibody is conjugated to monomethyl auristatin E or an analog, derivative or prodrug thereof. In some embodiments, the antibody is conjugated to monomethyl auristatin F or an analog, derivative or prodrug thereof. In some embodiments, the antibody is conjugated to pyrrolo[2,1-c][1,4]-benzodiazepine or an analog, derivative or prodrug thereof. In some embodiments, the antibody is conjugated to irinotecan or an analog, derivative or prodrug thereof.

The invention will be further illustrated by the figures and following examples. However, these examples and figures should not be interpreted in any way as limiting the scope of the present invention.

EXAMPLES

Materials and Methods

Material

Human Samples

Blood was collected at the Etablissement Français du Sang (Nantes, France). Heparinized blood samples were taken from healthy volunteers after signing an informed consent approved by the ethical committee of relevant institutions (#No CPDL-PLER-2018 180).

The gender of the donors was not available.

Methods

Peptides Libraries 16-aa peptides were randomly designed on human MHC-II alleles based on their alignment with rat sequence (Genscript, USA). Purity was >90%. Human peptides were dissolved and conserved as described above and diluted at 120 μg/ml in Texmacs medium for use in vitro.

Cell Purification

PBMCs were isolated by FICOLL-PAQUE™ density-gradient centrifugation at 2000 rpm for 20 min at room temperature without brake. Remaining red blood cells and platelets were removed using 5 min incubation with a hypotonic solution and centrifugation at 1000 rpm for 10 min at 4° C. For pDC and T cell sorting, B cells, monocytes and NK cells were magnetically depleted (DYNABEADS®, Invitrogen) by using anti-CD19 (clone: HBI19, eBiosciences), anti-CD14 (clone: M5E2, eBiociences) and anti-CD16 (Clone: 3G8, purified) mAbs respectively. Enriched PBMCs were stained with anti-CD45RC-FITC (clone: MT2, IQ-Products), anti-CD8α-PE-Cy7 (clone: RPT8, eBiociences) and anti-Nrp1-PE (clone: u21-1283, BD Biosciences) for sorting of $CD8\alpha^+CD45RC^{low}$ Tregs and Neurophilin-$1^+$ pDCs. Enriched PBMCs were stained with anti-CD3-PeCy7 (clone SK7, BD Biosciences), anti-CD4-PerCP-Cy5.5 (clone: RPA-T4, BD Biosciences) and anti-CD25- APC-Cy7 (clone: M-A251, BD Biosciences) mAbs for sorting of $CD4^+$ $CD25^-$ Teff cells. APCs were obtained from PBMCs by either magnetically depleting T cells with an anti-CD3 (OKT3 purified, 5 μg/ml) mAb (for stimulation of Teff in proliferation assays) or by gating out T cells during sorting using anti-CD3-PE (clone: HIT3a, BD Biosciences) (for activation and expansion tests). FACS ARIA II (BD biosciences, Mountain View, CA) was used for sorting. Purity was greater than 98%.

Peptide Stimulation Assay $CD8^+CD45RC^{low}$ Treg cells and autologous pDCs from the same healthy HLA-$A2^+$ donor were co-cultured in serum-free Texmacs medium (Miltenyi Biotec) supplemented with IL-2 (25 U/ml, PROLEUKIN®, Novartis), CpG ODN 2006 (0.5 μM) and the different synthesized peptides (120 μg/ml) at a ratio 4:1 of Tregs:pDCs for 5 days. $CD8^+CD45RC^{low}$ Treg activation was analyzed based on expression of CD69 and CD25 markers. As negative control and in order to normalize the results, a negative peptide was used (ALIAPVHAV—SEQ ID NO: 14). Dapi was used as viability marker. As a positive control, $CD8^+CD45RC^{low}$ Tregs were stimulated with anti-CD3 (OKT3, 1 μg/ml) and anti-CD28 mAbs (clone: CD28.2; 1 μg/ml). Results were analyzed using the FACS Canto II cytometer (BD Biosciences) and Flowjo software (Tree Star, Inc. USA, version 10).

Suppression Assays

CFSE-labeled $CD4^+$ $CD25^-$ Teffs and $CD8^+CD45RC^{low}$ Tregs from the same healthy volunteer (HLA-$A2^+$) were co-cultured with a pool of allogeneic APCs from 3 different healthy donors (HLA-$A2^-$) in RPMI1640 medium supplemented with 5% human AB serum. Culture was done at 1:1:1 ratio (where $1=5\times10^4$ cells/well) for 5 days in triplicate in a V-bottom 96 well plate. Proliferation of $CD4^+$ $CD25^-$ responder T cells was analyzed by flow cytometry (FACS Canto II BD Biosciences™) by gating on $CD3^+CD4^+$ living cells (DAPI negative) and using Flowjo software (Tree Star, Inc. USA, version 10).

Extracellular and Intracellular Stainings

For the analysis of GITR (clone: DT5D3, Miltenyi Biotec), Foxp3 (clone:259D/C7, BD Biosciences), IL-10 (clone: JES3-9D7, BD Biosciences), IL-34 (clone: IC5265P, R&D), TGFβ1 (clone: TW4-9E7, BD Biosciences) and IFNγ (clone: B27, BD Biosciences), $CD8^+CD45RC^{low}$ Treg cells were stimulated with PMA (50 ng/ml) and ionomycin (1 μg/ml) for 5 h in presence of Brefeldin A (10 μg/ml) for the last 4 hours in Texmacs medium (Miltenyi Biotec). In order to select viable cells, Fixable Viability Dye eF506 (ThermoFisher Scientific) was used as viability marker. Fc receptors were blocked before staining (BD Biosciences) and cells were permeabilized with Fix/Perm kit (Ebiociences) for intracellular staining. Cell phenotype was analyzed by flow cytometry using the LSR II (BD Biosciences, Mountain View, CA) and Flowjo software (Tree Star. Inc. USA, version 10).

Expansion in vitro of human $CD8^+CD45RC^{low}$ Tregs $5\times10^5$ $CD8^+CD45RC^{low}$ Tregs and $2\times10^6$ autologous APCs from HLA-$A2^+$ healthy donors were seeded in a 24 well plate in Texmacs Medium (Miltenyi Biotec), supplemented with penicillin (100 U/ml), streptomycin (100 μg/ml), rhIL-2 (1000 U/ml, PROLEUKIN®, Novartis), rhIL-15 (1Ong/ml, Miltenyi Biotec), CpG (0.5 μM), and the different peptides (120 μg/ml) derived from HLA-II molecule (GenScript). As negative control, a negative irrelevant peptide (ALIAPVHAV—SEQ ID NO: 14) was used. As a positive control, $CD8^+CD45RC^{low}$ Tregs were stimulated with plate-coated anti-CD3 (clone: OKT3, 1 μg/ml) mAb and soluble anti-CD28 mAb (clone: CD28.2; 1 μg/ml). At day 7, Tregs were counted and re-expanded. Cytokines were freshly added twice a week. Finally, at day 14, cells were used for experiments.

Quantification and Statistical Analysis

For the peptide activation test, a non-parametric Wilcoxon signed-rank test, comparing column median to a hypothetical value of 1.0, was done. Analyses were made with GraphPad Prism 7 software (GraphPad).

Results

Four 16aa peptides were designed from four random human MHC class II alleles based on the sequences of the Du51 peptide (NREEYARFDSDVGEYR) and the overlapping 12-mer peptide Bu31-10 (YLRYDSDVGEYR) both bearing the SDVGEYR motif at C-term end (FIG. 1): Hpep1 (NQEESVRFDSDVGEFR—SEQ ID NO: 1), Hpep2 (NREEYARFDSDVGEFR—SEQ ID NO: 2), Hpep3 (NREEYARFDSDVGVYR—SEQ ID NO: 3) and Hpep4 (NREEYVRFDSDVGEYR—SEQ ID NO: 4). We individually tested these peptides differing at positions 2, 5, 6, 14 or 15 in a 5-days culture assay using and syngeneic $CD8^+$ $CD45RC^{low}$ Tregs and autologous HLA-$A2^+$ pDCs from the same individuals in presence of interleukin-2 (IL-2) and CpG oligodeoxynucleotides (or CpG ODN) in serum free Texmacs medium (FIG. 2). As shown on FIGS. 3A-C, CD25 and CD69 expression was upregulated on Tregs following incubation with Hpep1, Hpep2 and Hpep4 peptides. These three peptides share the conserved SDVGE-X-R (SEQ ID NO: 13) 7aa motif while Hpep3 has in addition a valine (V) in place of the glutamic acid (E) at position 14 of the peptide, probably impacting TCR recognition.

From these peptides, shorter peptides were further identified: NREEYARFD (SEQ ID NO: 5), REEYARFDS (SEQ ID NO: 6), EEYARFDSD (SEQ ID NO: 7), EYARFDSDV (SEQ ID NO: 8), YARFDSDVG (SEQ ID NO: 9), ARFDSDVGE (SEQ ID NO: 10), RFDSDVGEF (SEQ ID NO: 11) and FDSDVGEFR (SEQ ID NO: 12).

Figure 4:
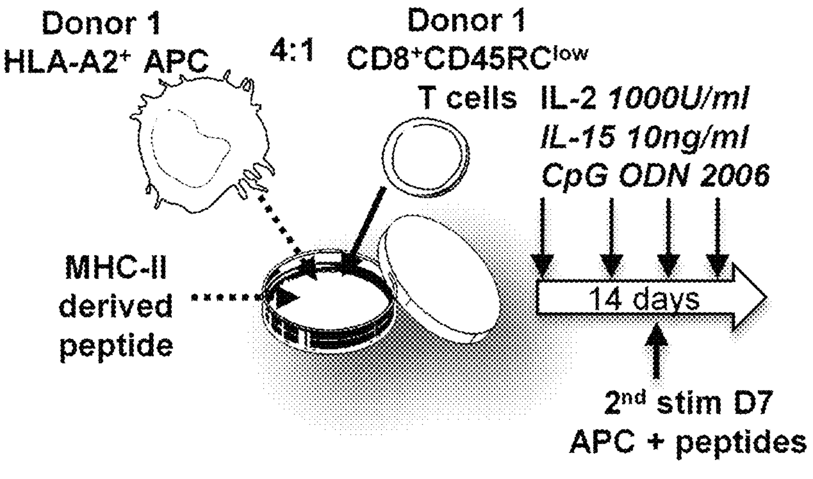
FIG. 4 is a scheme depicting the protocol of $CD8^+$ Treg expansion by Hpep2 peptide. CD8 Tregs were stimulated at day 0 and day 7 by syngeneic $HLA\text{-}A2^+$ APCs, Hpep2 peptide, IL-2, IL-15 and CpG ODN. Cytokines were added twice a week.
Figure 5:
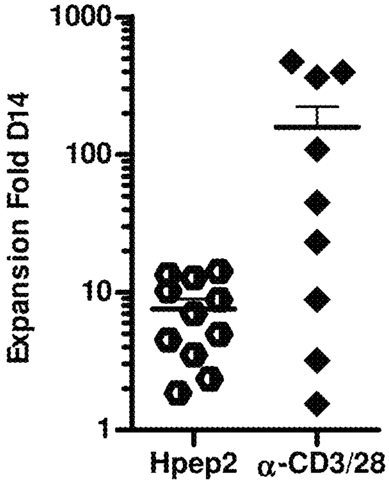
FIG. 5 is a graph showing the total Treg fold expansion after 14 days culture with Hpep2 or anti-CD3/anti-CD28 mAbs (versus day 0).
Figure 6A:
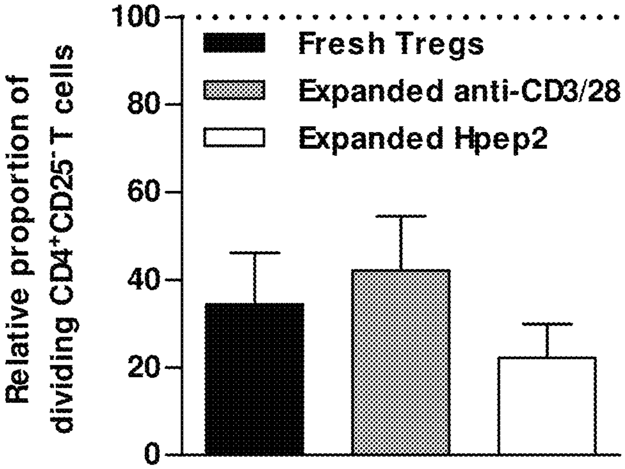
FIGS. 6A to 6E shows the suppressive activity of $CD8^+$ $CD45RC^{low}$ Tregs. 6A is a graph showing the proportion of dividing $CD4^+$ $CD25^-$ T cells co-cultured with $CD8^+$ $CD45RC^{low}$ Tregs from the same donor. After 14 days of Hpep2 peptide or polyclonal stimulation, expanded Tregs were tested for suppressive activity on syngeneic CFSE-labeled $CD4^+$ $CD25^-$ T cells stimulated with allogeneic APCs pooled from 3 healthy volunteers, as compared to fresh Tregs. n=2 to 5. 6B, 6C, 6D and 6E are representative histograms of CFSE staining in the conditions mentioned above: control condition without $CD8^+CD45RC^{low}$ Tregs (6B); in presence of $CD8^+CD45RC^{low}$ Tregs expanded with the Hpep2 peptide (6C); in presence of $CD8^+CD45RC^{low}$ Tregs expanded with anti-CD3/anti-CD28 mAbs (polyclonal stimulation) (6D); in presence of fresh $CD8^+$ $CD45RC^{low}$ Tregs (6E).
Figures 6B, 6C, 6D, 6E:
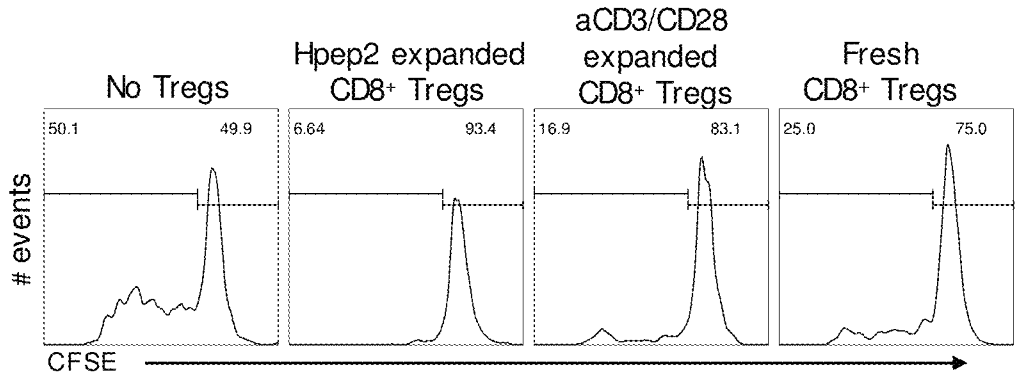
Figure 7:
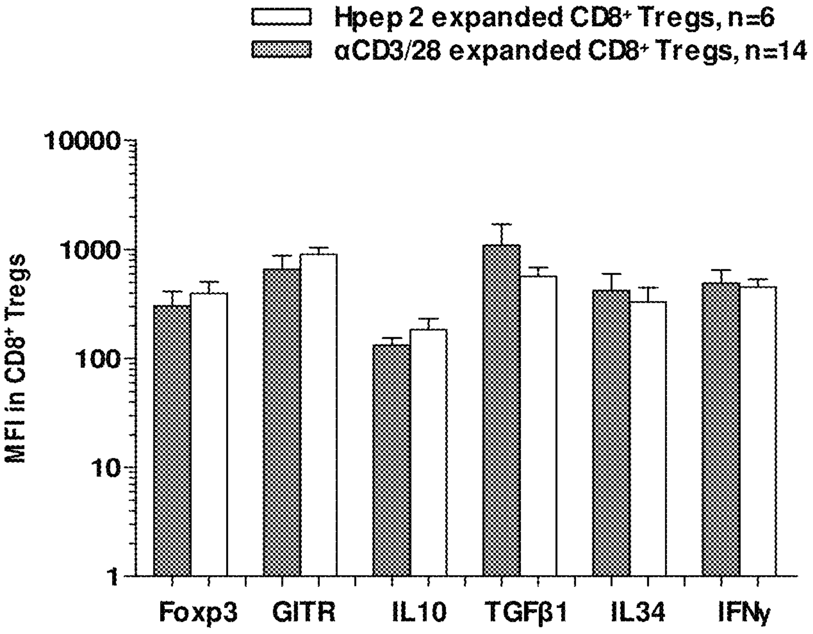
FIG. 7 is a graph showing that Hpep2-expanded $CD8^+$ $CD45RC^{low}$ Tregs display similar markers expression compared to polyclonally expanded $CD8^+CD45RC^{low}$ Tregs. $CD8^+$ Tregs were expanded for 14 days with Hpep2 or anti-CD3/anti-CD28 mAbs and analyzed by flow cytometry for Foxp3, GITR, IL-10, TGFβ1, IL-34 and IFNγ expression levels. n=6 to 14.

To determine whether $CD8^+CD45RC^{low}$ Tregs could be expanded using this MHC-II derived peptide, an expansion protocol was set up using sorted $CD8^+CD45RC^{low/-}$ Tregs and APCs from the same individual with the Hpep2 peptide in presence of IL-2, IL-15 and CpG ODN and compared to a polyclonal stimulation (anti-CD3/28) in similar conditions (FIG. 4). Expansion with APCs and Hpep2 resulted in a 10-fold expansion of the CD8$^+$CD45RC$^{low}$ Tregs in 14 days (FIG. 5), although actual expansion of the small Hpep2-specific Treg fraction present at day 0 may be much higher. Importantly, as shown on FIGS. 6A-E, both Hpep2 and anti-CD3/28 expanded CD8$^+$CD45RC$^{low}$ Tregs were efficient at suppressing an allogeneic immune response, similarly to fresh CD8$^+$CD45RC$^{low}$ Tregs. Interestingly, peptide-stimulated Tregs tend to be more suppressive than polyclonal Tregs, suggesting the potential benefit of expanding antigen-specific Tregs for therapy. As shown on FIG. 7, no significant differences were observed in the level of expression of Foxp3, GITR, IL-10, IFNγ and IL-34 in Hpep2 or anti-CD3/28 expanded CD8$^+$CD45RC$^{low}$ Tregs.

Altogether, this suggest that human HLA class II peptides bearing the consensus SDVGE-X-R (SEQ ID NO: 13) 7aa motif can efficiently activate and expand suppressive human CD8$^+$ Tregs.

REFERENCES

Throughout this application, various references describe the state of the art to which this invention pertains. The disclosures of these references are hereby incorporated by reference into the present disclosure.

The invention claimed is:

1. An immunoconjugate comprising an antibody conjugated or fused to an isolated peptide of sequence NQEESVRFDSDVGEFR (Hpep 1—SEQ ID NO:1), wherein the antibody is directed against a surface antigen of an antigen presenting cell.

2. A nanoparticle comprising an isolated peptide of sequence NQEESVRFDSDVGEFR (Hpep 1—SEQ ID NO:1).

3. The nanoparticle according to claim 2, wherein said nanoparticle is a liposome.

4. A vaccine composition comprising the immunoconjugate according to claim 1.

5. A medicament comprising the immunoconjugate according to claim 1.

6. A method for reducing transplant or graft rejection or graft versus host disease (GVHD) in a patient in need thereof, said method comprising administering to the patient the immunoconjugate according to claim 1.

7. A vaccine composition comprising the nanoparticle according to claim 1.

8. A medicament comprising the nanoparticle according to claim 2.

9. A method for reducing transplant or graft rejection or graft versus host disease (GVHD) in a patient in need thereof, said method comprising administering to the patient the nanoparticle according to claim 2.

* * * * *

SEQUENCE LISTING

```
<160> NUMBER OF SEQ ID NOS: 17

<210> SEQ ID NO 1
<211> LENGTH: 16
<212> TYPE: PRT
<213> ORGANISM: Homo sapiens

<400> SEQUENCE: 1

Asn Gln Glu Glu Ser Val Arg Phe Asp Ser Asp Val Gly Glu Phe Arg
1               5                   10                  15


<210> SEQ ID NO 2
<211> LENGTH: 16
<212> TYPE: PRT
<213> ORGANISM: Homo sapiens

<400> SEQUENCE: 2

Asn Arg Glu Glu Tyr Ala Arg Phe Asp Ser Asp Val Gly Glu Phe Arg
1               5                   10                  15


<210> SEQ ID NO 3
<211> LENGTH: 16
<212> TYPE: PRT
<213> ORGANISM: Homo sapiens

<400> SEQUENCE: 3

Asn Arg Glu Glu Tyr Ala Arg Phe Asp Ser Asp Val Gly Val Tyr Arg
1               5                   10                  15


<210> SEQ ID NO 4
<211> LENGTH: 16
<212> TYPE: PRT
<213> ORGANISM: Homo sapiens

<400> SEQUENCE: 4

Asn Arg Glu Glu Tyr Val Arg Phe Asp Ser Asp Val Gly Glu Tyr Arg
1               5                   10                  15


<210> SEQ ID NO 5
<211> LENGTH: 9
<212> TYPE: PRT
<213> ORGANISM: Homo sapiens

<400> SEQUENCE: 5

Asn Arg Glu Glu Tyr Ala Arg Phe Asp
1               5


<210> SEQ ID NO 6
<211> LENGTH: 9
<212> TYPE: PRT
```

<213> ORGANISM: Homo sapiens

<400> SEQUENCE: 6

Arg Glu Glu Tyr Ala Arg Phe Asp Ser
1 5

<210> SEQ ID NO 7
<211> LENGTH: 9
<212> TYPE: PRT
<213> ORGANISM: Homo sapiens

<400> SEQUENCE: 7

Glu Glu Tyr Ala Arg Phe Asp Ser Asp
1 5

<210> SEQ ID NO 8
<211> LENGTH: 9
<212> TYPE: PRT
<213> ORGANISM: Homo sapiens

<400> SEQUENCE: 8

Glu Tyr Ala Arg Phe Asp Ser Asp Val
1 5

<210> SEQ ID NO 9
<211> LENGTH: 9
<212> TYPE: PRT
<213> ORGANISM: Homo sapiens

<400> SEQUENCE: 9

Tyr Ala Arg Phe Asp Ser Asp Val Gly
1 5

<210> SEQ ID NO 10
<211> LENGTH: 9
<212> TYPE: PRT
<213> ORGANISM: Homo sapiens

<400> SEQUENCE: 10

Ala Arg Phe Asp Ser Asp Val Gly Glu
1 5

<210> SEQ ID NO 11
<211> LENGTH: 9
<212> TYPE: PRT
<213> ORGANISM: Homo sapiens

<400> SEQUENCE: 11

Arg Phe Asp Ser Asp Val Gly Glu Phe
1 5

<210> SEQ ID NO 12
<211> LENGTH: 9
<212> TYPE: PRT
<213> ORGANISM: Homo sapiens

<400> SEQUENCE: 12

Phe Asp Ser Asp Val Gly Glu Phe Arg
1 5

<210> SEQ ID NO 13
<211> LENGTH: 7
<212> TYPE: PRT
<213> ORGANISM: Homo sapiens
<220> FEATURE:

-continued

```
<221> NAME/KEY: SITE
<222> LOCATION: 6
<223> OTHER INFORMATION: Xaa refers to any amino acid

<400> SEQUENCE: 13

Ser Asp Val Gly Glu Xaa Arg
1               5


<210> SEQ ID NO 14
<211> LENGTH: 9
<212> TYPE: PRT
<213> ORGANISM: Artificial Sequence
<220> FEATURE:
<223> OTHER INFORMATION: Negative peptide

<400> SEQUENCE: 14

Ala Leu Ile Ala Pro Val His Ala Val
1               5


<210> SEQ ID NO 15
<211> LENGTH: 16
<212> TYPE: PRT
<213> ORGANISM: Artificial Sequence
<220> FEATURE:
<223> OTHER INFORMATION: Du51 peptide

<400> SEQUENCE: 15

Asn Arg Glu Glu Tyr Ala Arg Phe Asp Ser Asp Val Gly Glu Tyr Arg
1               5                   10                  15


<210> SEQ ID NO 16
<211> LENGTH: 12
<212> TYPE: PRT
<213> ORGANISM: Artificial Sequence
<220> FEATURE:
<223> OTHER INFORMATION: Bu31-10

<400> SEQUENCE: 16

Tyr Leu Arg Tyr Asp Ser Asp Val Gly Glu Tyr Arg
1               5                   10


<210> SEQ ID NO 17
<211> LENGTH: 7
<212> TYPE: PRT
<213> ORGANISM: Artificial Sequence
<220> FEATURE:
<223> OTHER INFORMATION: MHC-derived human motif

<400> SEQUENCE: 17

Ser Asp Val Gly Glu Tyr Arg
1               5
```